United States Patent [19]

Lafferty et al.

[11] Patent Number: 5,006,521
[45] Date of Patent: Apr. 9, 1991

[54] α-ADRENERGIC RECEPTOR ANTAGONISTS AND METHODS OF USE THEREAS

[75] Inventors: John J. Lafferty, Levittown; Robert M. DeMarinis, Ardmore; Dinubhai H. Shah, Norristown, all of Pa.

[73] Assignee: SmithKline Beecham Corporation, Philadelphia, Pa.

[21] Appl. No.: 492,696

[22] Filed: Mar. 13, 1990

Related U.S. Application Data

[63] Continuation of Ser. No. 361,875, Jun. 6, 1989, abandoned, which is a continuation-in-part of Ser. No. 201,005, Jun. 1, 1988, abandoned.

[51] Int. Cl.$^5$ .................... C07D 459/06; A61K 31/38
[52] U.S. Cl. ..................... 514/215; 540/495; 514/217
[58] Field of Search .................. 514/215, 217; 540/495

[56] References Cited

U.S. PATENT DOCUMENTS 3,833,591 9/1974 McManus .................. 260/239 R
3,904,645 9/1975 McManus .................. 260/326.5 B
3,906,000 9/1975 McManus .................. 260/326.5

4,469,634 9/1984 DeMarinis .................. 260/239 BB

FOREIGN PATENT DOCUMENTS 8700522 1/1987 PCT Int'l Appl. .

Primary Examiner—David B. Springer
Attorney, Agent, or Firm—Mary E. McCarthy; Stuart R. Suter; Edward T. Lentz

[57] ABSTRACT

Alpha-adrenoceptor antagonists having the formula:

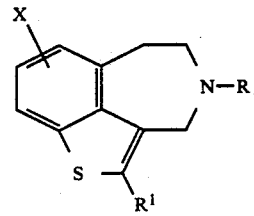

which are useful to produce α-adrenoceptor antagonism, pharmaceutical compositions including these antagonists, and methods of using these antagonists to produce α-adrenoceptor antagonism in mammals.

19 Claims, No Drawings

α-ADRENERGIC RECEPTOR ANTAGONISTS AND METHODS OF USE THEREAS

This is a continuation of application Ser. No. 07/361,875, filed June 6, 1989, now abandoned, which is a continuation-in-part of application Ser. No. 07/201,005, filed June 1, 1988, now abandoned.

FIELD OF THE INVENTION

This invention relates to novel 2-substituted-3,4,5,6-tetrahydrothieno[4,3,2-ef][3]benzazepine compounds that are α-adrenergic receptor antagonists.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: α and β. Based upon selectivity of the receptors for a series of agonists and antagonists, the α adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, J. Med. Chem., 25, 1389 (1982)). Experiments using 6-chloro-9-(3-methyl-2-butenyloxy)-3-methyl-2,3,4,5-tetrahydro-lH-3-benzazepine (SK&F 104078) demonstrated that the classical adrenoceptors are heterogeneous and can be divided into SK&F 104078—insensitive and SK&F 104078—sensitive $\alpha_2$ adrenoceptors. The latter variously are referred to as postjunctional $\alpha_2$ adrenoceptors or, preferably, $\alpha_3$ adrenoceptors, U.S. Pat. No. 4,683,229, July 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with α adrenoceptors include methyldopa, clonidine, and prazosin. Efforts to modulate sympathetic tone through interactions with α adrenoceptors have resulted in several compounds that interact somewhat selectively with $\alpha_1$ or $\alpha_2$ adrenoreceptors. Selective agonists include phenylephrine and methoxamine which preferentially activate $\alpha_1$ receptors; and clonidine, α-methyl-norepinephrine, and tramazoline which preferentially activate $\alpha_2$ adrenoceptors. Examples of selective α-adrenoceptor antagonists include prazosin which has high selectivity for $\alpha_1$ adrenoceptors; and the $\alpha_2$-selective blockers yohimbine and rauwolscine.

U.S. Pat. No. 4,469,634, dated Sept. 4, 1984, describes allyloxy- and allythio-2,3,4,5-tetrahydro-lH-3-benzazepines useful as intermediates for preparing $\alpha_2$ adrenoceptor affinity resins and as antihypertensive agents.

U.S. Pat. Nos. 3,833,591, 3,904,645, and 3,906,000 disclose substituted compounds of the following base structure:

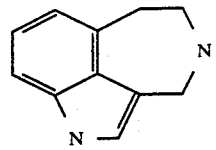

These compounds are useful as hypoglycemic agents.

PCT Application Number WO 87/00522 describes a series of 4-aminotetrahydrobenz[c,d]indoles and tetrahydroazepino[3,4,5-c,d]indoles having the general formula:

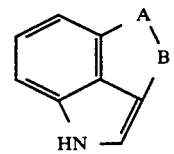

in which A-B is —CH$_2$—CH(NRR)—CH$_2$ or —CH$_2$—CH$_2$—NR—CH$_2$. These compounds are dopamine agonists useful as hypotensives.

SUMMARY OF THE INVENTION

The present invention resides in the discovery that various 2-substituted-3,4,5,6-tetrahydrothieno-[4,3,2-ef][3]benzazepine compounds are α-adrenoceptor antagonists or are useful in preparing α-adrenoceptor antagonists. Presently preferred compounds of the invention include:
7-chloro-3,4,5,6-tetrahydro-4-methylthieno[4,3,2-ef][3]benzazepine-2-methanol;
7-chloro-3,4,5,6-tetrahydro-4-methylthieno[4,3,2-ef][3]benzazepine-2-carboxaldehyde;
methyl 7-chloro-3,4,5,6-tetrahydro-4-methylthieno-[4,3,2-ef][3]benzazepine-2-carboxylate;
ethyl 7-chloro-3,4,5,6-tetrahydro-4-methylthieno-[4,3,2-ef][3]benzazepine-2-carboxylate;
7-chloro-3,4,5,6-tetrahydro-4-methyl-2-[(2-propenyloxy)methyl]thieno[4,3,2-ef][3]benzazepine;
7-chloro-3,4,5,6-tetrahydro-4-methylthieno-[4,3,2-ef][3]benzazepine;
7-chloro-3,4,5,6-tetrahydro-2,4-dimethylthieno[4,3,2-ef][3]benzazepine;
7-chloro-3,4,5,6-tetrahydro-4-methylthieno-[4,3,2-ef][3]benzazepine-2-ethan-2-ol;
7-chloro-3,4,5,6-tetrahydro-4-methylthieno-[4,3,2-ef][3]benzazepine-2-ethan-2-one;
7-chloro-3,4,5,6-tetrahydro-4-methylthieno-[4,3,2-ef][3]benzazepine-2-carboxamide;
N,N-dimethyl-7-chloro-3,4,5,6-tetrahydro-4-methylthieno[4,3,2-ef][3]-2-benzazepine-carboxamide;
7-chloro-3,4,5,6-tetrahydro-4-methyl-2-(1-methylethyl)thieno[4,3,2-ef][3]benzazepine;
7-chloro-2-ethyl-3,4,5,6-tetrahydro-4-methyl-thieno[4,3,2-ef][3]benzazepine;
7-chloro-2-propyl-3,4,5,6-tetrahydro-4-methyl-thieno[4,3,2-ef][3]benzazepine; and
2,7-dichloro-3,4,5,6-tetrahydro-4-methyl-thieno[4,3,2-ef][3]benzazepine.

In a further aspect of the invention there are provided methods of antagonizing α adrenoceptors in mammals, including humans, that comprise administering internally to a subject an effective amount of a 2-substituted- 3,4,5,6-tetrahydrothieno[4,3,2-ef]-[3]benzazepine compound.

Included in the present invention are pharmaceutical compositions that include compounds useful in the method of the invention and a suitable pharmaceutical carrier. Preferably, these compositions are used to produce α-adrenoceptor antagonism and contain an effective amount of compounds useful in the methods of the invention.

DETAILED DESCRIPTION OF THE INVENTION

The presently invented compounds that are α-adrenoceptor antagonists or are useful in preparing α-adrenoceptor antagonists are represented by the following Formula (I):

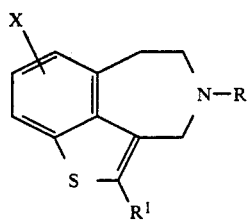

(I)

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, $SCF_3$, or any accessible combination thereof of up to three substituents;

R is H, $C_{1-6}$alkyl, or $C_{3-5}$alkenyl;

$R^1$ is W, $(CH_2)_{0-2}CWYZ$, or $C_{3-5}$alkenyl, except where the double bond is in the 1-position;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$; each $R^{13}$ independently is H or $C_{1-6}$alkyl;

$R^{14}$ and $R^{15}$ independently are $C_{1-6}$alkyl or $(CH_2)_{0-6}$aryl;

W is H, $NO_2$, $C_{1-6}$alkyl, $CH_2CH_2OH$, CN, $C(R^3)_2(OR^2)$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I, $CF_3$, or $(CH_2)_{0-6}$aryl;

Y and Z independently are H or $C_{1-6}$alkyl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

As used herein $C_{1-6}$alkyl means straight or branched alkyl of one to six carbon atoms, $C_{3-5}$alkenyl means a straight or branched chain alkenyl having from 3 to 5 carbon atoms, aryl means a phenyl group which is unsubstituted or is substituted by $C_{1-6}$alkyl, $C_{1-6}$alkoxy, halo, $CF_3$, or CN, and "any accessible combination thereof" means any combination of up to three substituents on the phenyl moiety that is available by chemical synthesis and is stable.

Formula (Ia) includes presently preferred Formula (I) compounds:

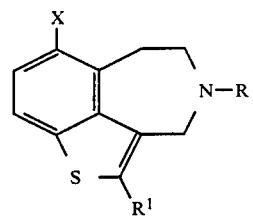

(Ia)

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, or $SCF_3$;

R is H, $C_{1-6}$alkyl, or $C_{3-5}$alkenyl;

$R^1$ is W, $(CH_2)_{0-2}CWYZ$, or $C_{3-5}$alkenyl, except where the double bond is in the 1-position;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

each $R^{13}$ independently is H or $C_{1-6}$alkyl;

$R^{14}$ and $R^{15}$ independently are $C_{1-6}$alkyl or $(CH_2)_{0-6}$aryl;

W is H, $NO_2$, $C_{1-6}$alkyl, $CH_2CH_2OH$, CN, $C(R^{13})_2(OR^2)$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I, $CF_3$, or $(CH_3)_{0-6}$aryl;

Y and Z independently are H or $C_{1-6}$alkyl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

Compounds of Formula (I) are prepared by the synthetic pathways shown in Schemes I through IV. In Schemes I through IV, W, X, Y, and Z are as defined in Formula (I).

SCHEME I

Method A

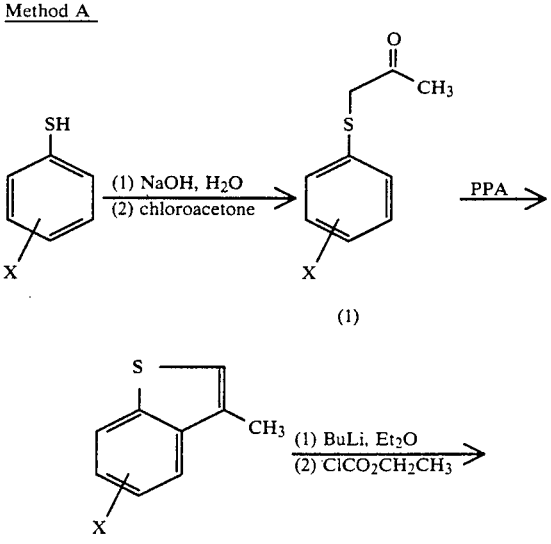

-continued
SCHEME I
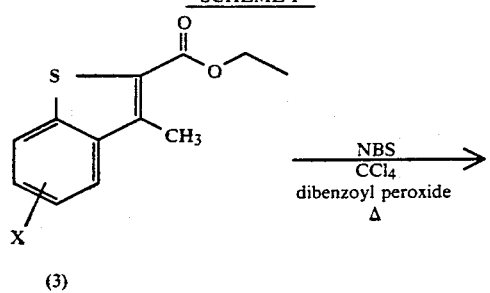
(3)
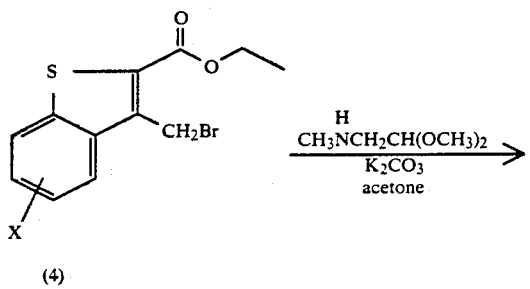
(4)
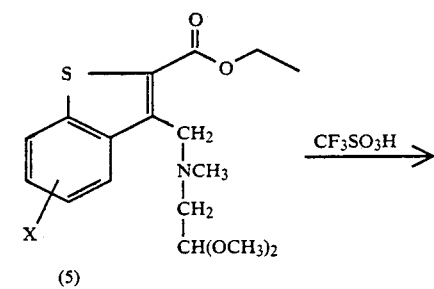
(5)
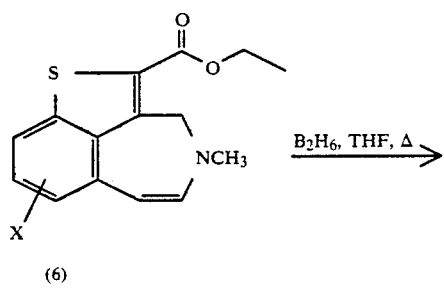
(6)
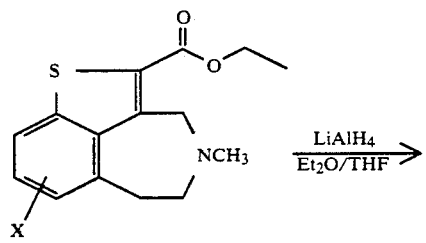
(7)
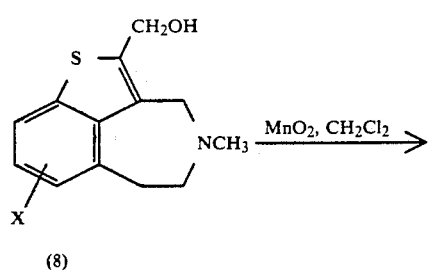
(8)
-continued
SCHEME I
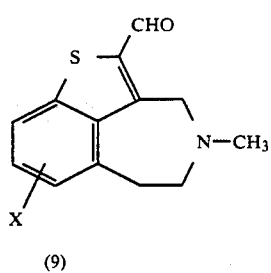
(9)
Method B
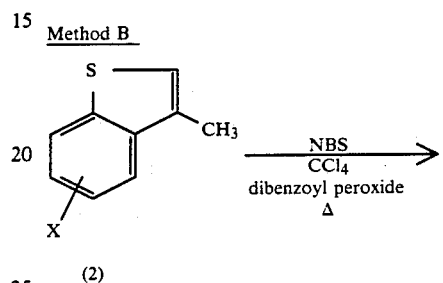
(2)
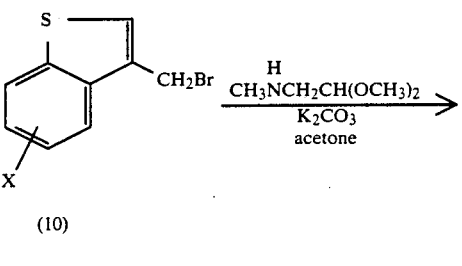
(10)
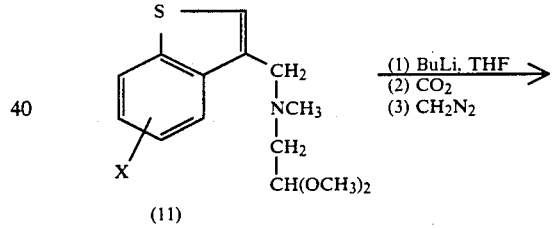
(11)
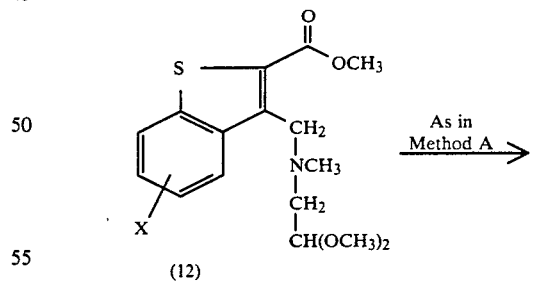
(12)
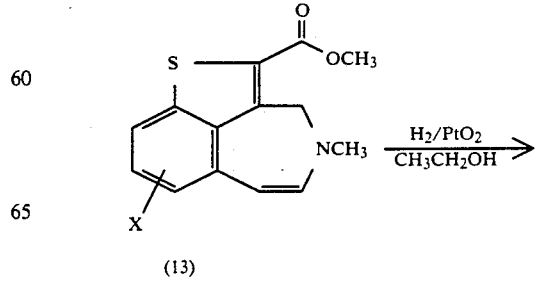
(13)

-continued
SCHEME I

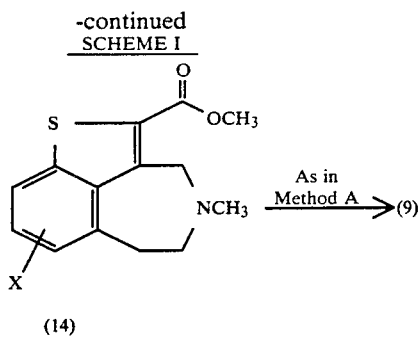

(14)

Scheme I, Method A, shows the synthesis of Formula (I) compounds in which the 2-position substituent is $CO_2CH_2CH_3$, CHO and $CH_2OH$, which are α-adrenoceptor antagonists and which are also useful as intermediates in synthesis of other Formula (I) compounds. According to Scheme I, thiophenol or a substituted thiophenol is treated with a base such as sodium hydroxide in a suitable solvent such as water. The resulting sodium thiophenolates are heated at 0° C. to 75° C., preferably 25° C., with a haloacetone, preferably chloroacetone to yield (phenylthio)propanones (1). Substituted benzo[b]thiophene formula (2) compounds are prepared by treating formula (1) compounds with a strong acid, preferably polyphosphoric acid (PPA), at from 0° C. to 175° C., preferably 25° C. to 130° C.

Formula (2) compounds are treated with a base, preferably butyllithium, in an inert solvent, preferably ethyl ether, at a suitable temperature, preferably 0° C., and then with an alkyl chloroformate, preferably ethyl chloroformate, at a suitable temperature, preferably 0° C., to produce formula (3) compounds.

Formula (3) compounds are treated with a halogenating agent, preferably N-bromosuccinimide (NBS), and an initiator, preferably dibenzoylperoxide, in an inert organic solvent, preferably carbon tetrachloride ($CCl_4$), preferably at reflux, to produce formula (4) compounds. Formula (5) compounds are prepared by dissolving formula (4) compounds in an organic solvent such as acetone and adding a suitable base, preferably potassium carbonate ($K_2CO_3$), and an N-($C_{1-6}$alkyl)-aminoacetaldehyde di($C_{1-4}$alkyl) acetal, preferably methylaminoacetaldehyde dimethyl acetal.

Formula (5) compounds are treated with acid, preferably trifluoromethanesulfonic acid, to yield enamine compounds of formula (6). Formula (6) compounds are treated with a reducing agent, preferably diborane, in an inert organic solvent, such as tetrahydrofuran, at a suitable temperature, such as at reflux, or reduced catalytically with a suitable catalyst, preferably platinum oxide, in a suitable solvent, preferably ethanol, to give benzazepine compounds of formula (7).

Thereafter, formula (7) compounds are added to a suitable reducing agent, preferably lithium aluminum hydride (LAH), in an inert solvent, preferably ethyl ether, to yield formula (8) compounds. Formula (8) compounds are treated with a suitable oxidizing agent, preferably manganese dioxide, in an inert solvent, preferably dichloromethane, to give benzazepine-2-carboxaldehyde compounds of formula (9).

Scheme I, Method B, shows the synthesis of Formula (I) compounds in which the 2-position substituent is $CO_2CH_3$. Formula (2) compounds are treated with a halogenating agent, preferably N bromosuccinimide (NBS), and an initiator, preferably dibenzoylperoxide, in an inert organic solvent, preferably carbon tetrachloride ($CCl_4$), preferably at reflux, to produce formula (10) compounds.

Formula (11) compounds are prepared by dissolving formula (10) compounds in an organic solvent, such as acetone, and adding a suitable base, preferably potassium carbonate ($K_2CO_3$), and an N-($C_{1-6}$alkyl)-aminoacetaldehy di($C_{1-4}$alkyl) acetal, preferably methylaminoacetaldehyde dimethyl acetal.

Formula (11) compounds are treated with a strong base, preferably butyllithium, in an inert solvent, such as ethyl ether, at a suitable temperature, preferably −30° C., and then with carbon dioxide to produce carboxylic acids which are treated with an alkylating agent, such as diazomethane, in an inert solvent, such as ethyl ether, to give formula (12) compounds.

Formula (12) compounds are converted to formula (13), formula (14), formula (8) and formula (9) compounds as described for Method A.

SCHEME II

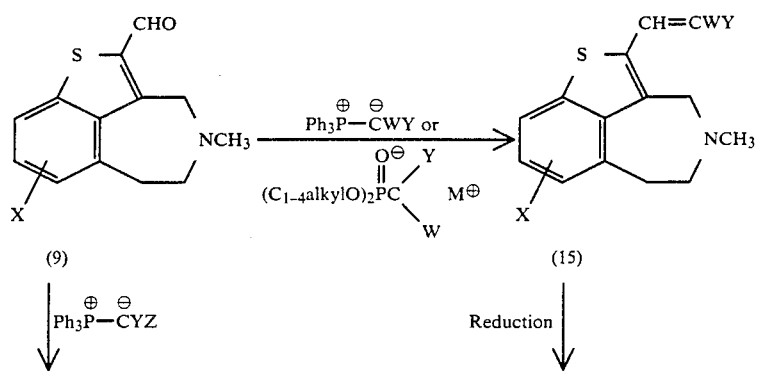

SCHEME II

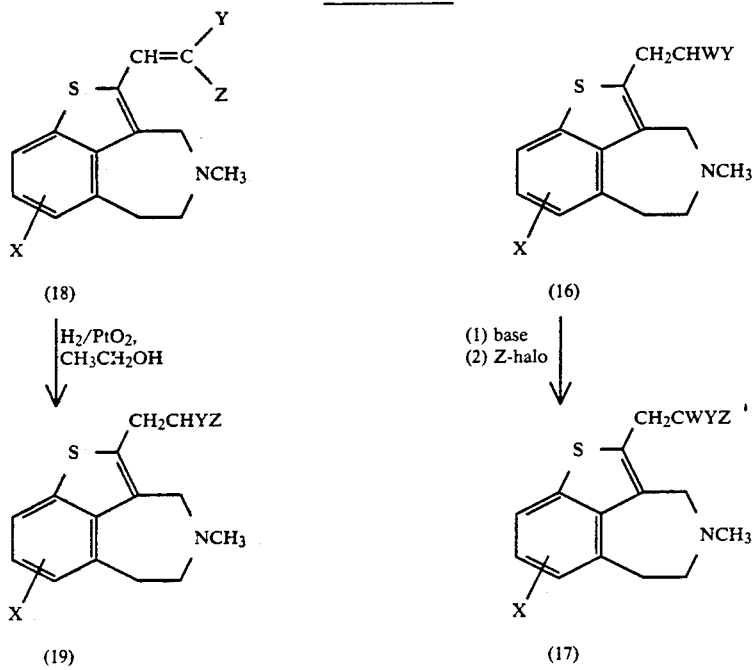

Scheme II shows synthesis of Formula (I) compounds in which the 2-position substituent is $CH_2CWYZ$. In Scheme II, X, W, Y and Z are as defined in Formula (I). According to Scheme II, formula (15) compounds are obtained from formula (9) compounds and a phosphonate or a phosphonium salt by treatment with a base, such as sodium hydride, in a suitable solvent, such as ethyl ether. The phosphonates or phosphonium salts are selected so that W and Y are the same as in the desired formula (17) compounds. The metal cation ($M^\oplus$) associated with the phosphonate is derived from the base used in this step on the synthesis. Suitable metal ions include lithium, sodium, and potassium.

Formula (15) compounds where W is CHO are prepared by reacting formula (9) compounds with a dialkyl phosphonoacetaldehyde dialkyl acetal, preferably diethyl phosphonoacetaldehyde diethyl acetal, followed by acid hydrolysis.

Formula (16) compounds where W is $CO_2R^5$, $COR^2$, $SOR^5$, $SO_2R^5$, $SO_3R^{12}$, $SO_2NR^3R^4$, $P(O)OR^3(OR^4)$, $P(O)R^5(OR^3)$, $P(O)R^5R^6$, $P(O)(OR^2)NR^3R^4$, $P(O)(NR^3R^4)_2$, or $P(O)R^5(NR^3R^4)$ are prepared by reduction of the corresponding formula (15) compounds with hydrogen and a suitable catalyst, preferably platinum oxide, in a suitable solvent, preferably ethanol.

Formula (15) compounds where W is CHO are reduced catalytically as the acetal followed by acid hydrolysis to produce formula (16) compounds wherein W is CHO.

Formula (16) compound where W is $NO_2$ or CN are prepared by reduction of the corresponding formula (15) compounds with a metal hydride, preferably sodium borohydride, in a suitable solvent, preferably isopropanol.

Formula (16) compounds where W is $CO_2H$ are prepared by hydrolyzing formula (16) compounds where W is $CO_2R^5$ with a strong acid, preferably hydrochloric acid in acetic acid. Formula (16) compounds where W is $CONR^3R^4$ are prepared from Formula (16) compounds where W is $CO_2H$ by treatment with a known halogenating agent, such as thionyl chloride, followed by reaction with an amine $HNR^3R^4$ or by treatment of a formula (16) compound where W is $C_2R^5$ with an amine $HNR^3R^4$.

Formula (16) compounds may be converted to formula (17) compounds by treatment with a strong base, such as lithium diisopropylamide, in a suitable inert solvent, preferably tetrahydrofuran, to give an anion which is alkylated with an alkyl halide or an alkyl sulfonate.

Formula (18) compounds are prepared from formula (9) compounds by treatment with an alkyltriphenylphosphonium salt, such as methyltriphenylphosphonium bromide, and a base, such as sodium hydride, in a suitable solvent, such as dimethylformamide and ethyl ether. The phosphonium salts are selected so that Y and Z are the same as in the desired formula (18) compounds. Formula (19) compounds are prepared from formula (18) compounds by reduction with hydrogen and a suitable catalyst, preferably platinum oxide, in a suitable solvent, such as ethanol.

SCHEME III

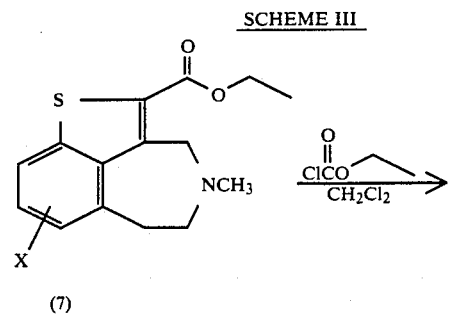

-continued
SCHEME III

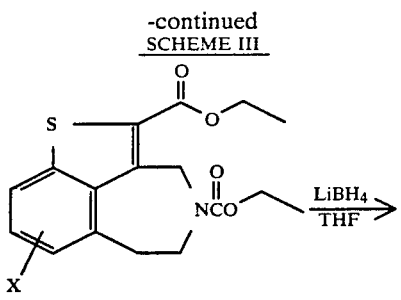
(20)

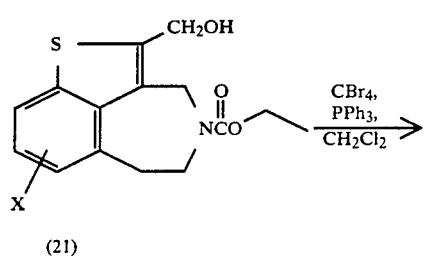
(21)

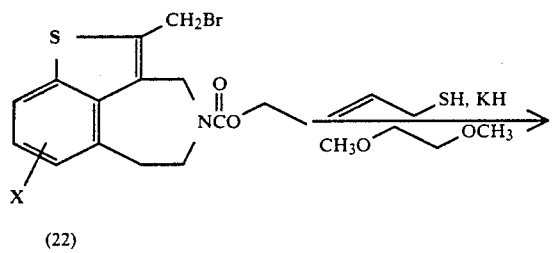
(22)

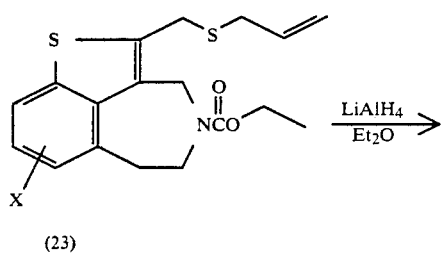
(23)

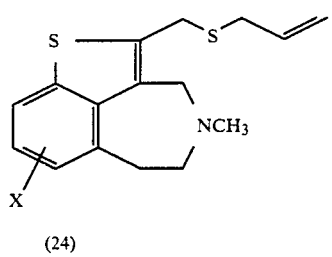
(24)

Scheme III shows formation of Formula (I) compounds in which the 2-position subsituent is W, CH₂CWYZ and CWYZ. In scheme III, X is as defined in Formula (I). According to Scheme III, formula (20) compounds are prepared from Scheme I, formula (7) compounds by treatment with a suitable haloformate, preferably ethyl chloroformate. Other haloformates, such as trichloroethyl chloroformate may also be employed. Formula (20) compounds are treated with a suitable reducing reagent, such as lithium borohydride, in a suitable solvent, preferably tetrahydrofuran, to give formula (21) compounds. Formula (22) compounds are prepared from formula (21) compounds by treatment with a suitable halogenating agent, such as carbon tetrabromide and triphenylphosphine, in a suitable solvent, preferably methylene chloride.

Formula (21) compounds also may be converted to chlorides or sulfonates by treatment with a suitable reagent, such as thionyl chloride or methanesulfonyl chloride, and a suitable base, such as triethylamine, in a suitable solvent, preferably methylene chloride. The halide or sulfonate group in formula (22) compounds may be displaced by a nucleophile, for example, cyanide ion, in a suitable solvent, such as acetonitrile, using a crown ether catalyst, such as 18-crown-6, to give Formula (I) compounds in which the 2-position substituent is CWYZ, where W is CN and Y and Z are each hydrogen atoms. This product may be elaborated further to produce Formula (I) compounds in which the 2-position substituent is CWYZ, where W is CN and Y and Z are each $C_{1-6}$alkyl or Y is a hydrogen atom and Z is a $C_{1-6}$alkyl group. These products may be formed by treatment of the above Formula (I) compounds with a strong base, such as lithium diisopropylamide, in a suitable inert solvent, preferably tetrahydrofuran, to give an anion which is alkylated with an alkyl halide or an alkyl sulfonate to produce the desired Formula (I) compounds.

Formula (I) compounds in which the 2-position substituent is (CH₂)₂CWYZ are formed in a fashion similar to that described for the preparation of compounds in which the 2-position substituent is CWYZ. In this case, the starting alcohol is a Scheme II, formula (17) compound in which W is CH₂OH and Y and Z are each hydrogen atoms. These formula (17) compounds may be converted to chlorides or sulfonates by treatment with a suitable reagent, such as thionyl chloride or methanesulfonyl chloride, and a suitable base, such as triethylamine, in a suitable solvent, preferably methylene chloride. The halide or sulfonate group may be displaced by a nucleophile, for example, cyanide ion, in a suitable solvent, such as acetonitrile, using a crown ether catalyst, such as 18-crown-6, to give Formula (I) compounds in which the 2-position substituent is (CH₂)₂CWYZ where W is CN and Y and Z are each hydrogen atoms. The desired Formula (I) compounds in which the 2-position substituent is (CH₂)₂CWYZ, where W is CN and Y and Z are each $C_{1-6}$alkyl or Y is a hydrogen atom and Z is a $C_{1-6}$ alkyl group, may be prepared from the above Formula (I) compounds by treatment with a strong base, such as lithium diisopropylamide, in a suitable inert solvent, preferably tetrahydrofuran, to give an anion which is alkylated with an alkyl halide or an alkyl sulfonate.

Formula (I) compounds in which the 2-position substituent is $C_{3-5}$alkenyl, except where the double bond is in the 1-position, may be prepared from Scheme II, formula (17) compounds, where Y and Z are each hydrogen atoms or Y is a hydrogen atom and Z is a $C_{1-6}$alkyl group and W is CH₂OH. These formula (17) compounds may be treated with a halogenating agent, such as thionyl chloride, and a suitable base, such as triethylamine, to give the corresponding halides. These compounds may be treated with a strong base, such as lithium diisopropylamide, to give the desired Formula (I) compounds in which the 2-position substituent is $C_{3-5}$alkenyl, except where the double bond is in the 1-position.

Formula (23) compounds are prepared from formula (22) compounds by treatment with an alkyl mercaptan and a suitable base, preferably potassium hydride, in a suitable solvent, such as 1,2-dimethoxyethane.

13

Formula (24) compounds are prepared from formula (23) compounds by reduction with a suitable reagent, preferably lithium aluminum hydride, in a suitable solvent, such as ethyl ether.

Compounds of formula (22) also may be treated with a variety of known nucleophiles, examples being: nitrogen compounds, such as nitrite; carbon compounds, such as t-butyl lithioacetate: sulfur compounds, such as sodium phenylsulfinate; and phosphorus compounds, such as triethylphosphite; to give Formula (I) compounds.

Scheme I, formula (8) compounds also may be treated with halogenating agents, such as thionyl chloride, to give halo compounds similar to formula (22) compounds where the ethoxycarbonyl group is replaced by a methyl group. Halo compounds obtained from formula (8) compounds may be treated with a variety of nitrogen, carbon, sulfur and phosphorus nucleophiles to give Formula (I) compounds directly.

SCHEME IV (20)

(25)

(26)

(27)

14

-continued
SCHEME IV

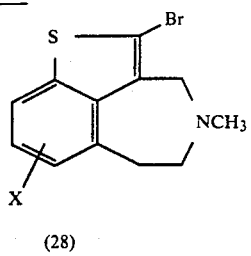

(28)

Scheme IV illustrates preparation of Formula (I) compounds in which the 2-position substituent is hydrogen or halo. In Scheme IV, X is as defined in Formula (I). According to Scheme IV, formula (20) compounds are hydrolyzed to formula (25) compounds with strong acid, preferably hydrochloric acid in acetic acid. Formula (25) compounds are decarboxylated, preferably by treatment with copper powder and quinoline, at a temperature of 150° to 250° C., preferably 200° C., to give formula (26) compounds. Formula (26) compounds are reduced with a suitable reagent, preferably lithium aluminum hydride, in a suitable solvent, such as ethyl ether, to yield formula (27) compounds. Formula (27) compounds are converted to hydrobromides and treated with a suitable brominating agent, preferably bromine, in a suitable solvent, such as aqueous acetic acid, to yield formula (28) compounds.

Formula (I) compounds in which the 2-position substituent is chloro are prepared in a similar way by treating formula (27) compounds as their hydrochlorides with chlorine.

Formula (I) compounds in which the 2-position substituent is phenyl or a $SR^5$ group are prepared from formula (27) compounds by treatment with a lithiating agent, such as butyl lithium, in a suitable solvent, such as tetrahydrofuran, to form the corresponding 2-lithio derivative. This intermediate is treated with a $(R^5)_2$-disulfide species, wherein $R^5$ is as defined in Formula (I) compounds, to form the 2-$SR^5$ compounds. Alternately, the 2-lithio intermediate is treated with a tri-alkyltin halide, such as tributyltin chloride, followed by reaction with an aryl halide, such as iodobenzene, in the presence of a palladium catalyst, such as bis(triphenylphosphine)palladium (II) chloride, to produce Formula (I) compounds wherein the 2-position substituent is phenyl.

Schemes I through IV outline preparation of Formula (I) compounds in which R is methyl. Formula (I) compounds wherein R is other than methyl are formed by selecting the N-($C_{1-6}$alkyl)aminoacetaldehyde di($C_{1-4}$alkyl)acetal used in preparing the formula (5) and (11) compounds of Scheme I so that the nitrogen is desirably substituted. Alternatively, Formula (I) compounds wherein R is other than methyl are prepared by reacting a Formula (I) compound wherein R is methyl with an alkyl haloformate, preferably trichloroethyl chloroformate, at approximately 50° C. to 100° C. to produce a trihaloalkyl carbamate. To this carbamate dissolved in a suitable organic solvent, such as tetrahydrofuran, is added an acid, preferably acetic acid, and a reducing agent, such as zinc dust, to yield a product in which R is hydrogen. This subsequently is reacted with a halo-$R^7$ compound, wherein $R^7$ is $C_{2-6}$alkyl or $C_{3-5}$alkenyl, to yield Formula (I) compounds wherein R is $C_{2-6}$alkyl or $C_{3-5}$alkenyl, respectively.

The substituted thiophenols and haloacetones used as starting materials in Scheme I are commercially available or can be synthesized from available materials by known methods. Additionally, the reactants used in Schemes I through IV are available or can be synthesized from available materials by known methods.

The pharmaceutically acceptable, nontoxic, acid addition salts having the utility of the free bases of Formula (I) are formed with inorganic or organic acids by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Because the compounds of Formula (I) are α-adrenoceptor antagonists they are useful in treating cardiovascular diseases in which changes in vascular resistance are desirable, including hypertension, pulmonary hypertension, congestive heart failure, myocardial ischemia, angina pectoris, and peripheral vascular disease. Formula (I) compounds also are useful in treating benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The α-adrenoceptor activity of certain compounds of the present invention was determined using the following in vitro systems.

Alpha$_1$ adrenoceptor antagonist activity was determined using the rabbit aorta. Male New Zealand White rabbits (2–4 Kg) were euthanized by cervical concussion. A 4 cm portion of the thoracic aorta was removed and placed in a dish of cold (10° C.) Krebs-Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force-displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6 μM) to block neuronal uptake and propranolol (1 μM) to block beta adrenoceptors. Tissues were usually challenged once with norepinephrine (0.1 μM) during the equilibration period to check for viability.

A cumulative concentration response curve to norepinephrine was obtained in each aortic segment. Following washout of norepinephrine, the α adrenoceptor antagonist to be tested was added to the bath. After the tissue had been in contact with the antagonist for 30–60 minutes, the norepinephrine concentration response-curve was repeated in the presence of antagonist. The tissue was then washed again, and a tenfold higher concentration of antagonist added. Following equilibration (30–60 minutes), a third norepinephrine concentration-response curve was determined in the presence of the antagonist.

The receptor dissociation constant ($K_B$) for the antagonist was determined using the relationship $$K_B = \frac{\text{Antagonist Concentration}}{\text{Dose Ratio} - 1}.$$

(Furchgott, R. F., *Handbook of Experimental Pharmacology*, eds. Eichler, et al., pp. 283–335 (Springer 1972)). The $K_B$ value obtained at each antagonist concentration was averaged to obtain a mean $K_B$ for each experiment.

Alpha$_2$ adrenoceptor antagonist activity of the compounds was determined using the isolated, superfused guinea pig left atrium. Briefly, the heart is removed from a pentobarbital-anesthetizei male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration-response curve for B-HT 920 (a known α$_2$ agonist) is prepared by administering increasing concentrations of B-HT 920 following each successive stimulation. The tissue then is superfused for thirty minutes with the α-adrenoceptor antagonist to be tested and the B-HT 920 concentration-effect curve is repeated in the presence of antagonist. Data are reported as $K_B$, defined above. Additional details of this test system are found in Hieble, J. P. and R. G. Pendleton, *Arch. Pharmacol.*, 309:217–224 (1979).

Alpha$_3$ adrenoceptor antagonist receptor activity was determined using the dog saphenous vein (DSV) as the test system. This test system has been shown a suitable preparation in which to characterize postsynaptic α$_2$ (α$_3$) adrenoceptors, Sullivan, A. T. and G. M. Drew, *Arch. Pharmacol.*, 314:249–58 (1980). This test system is prepared by removing the lateral saphenous vein from an anesthetized dog and cutting the vein into segments of 4 mm in length. Segments are mounted as described for the isolated rabbit aorta.

The α$_3$ adrenoceptor antagonist activity of the compounds of interest is determined by measuring shifts in the dose response curve of a specific agonist induced by the tested compounds. The α$_2$, α$_3$ agonist, B-HT 920, was used in testing the compounds listed in Table I.

Representative Formula (I) compounds which were tested using the above described in vitro test systems are listed in Table 1. Each of the compounds tested was found to have activity at one or more of the α adrenoceptor subtypes.

Table 1 ethyl 7-chloro-3,4,5,6-tetrahydro-4-methylthieno-[4,3,2-ef][3]benzazepine-2-carboxylate;

7-chloro-3,4,5,6-tetrahydro-4-methylthieno[4,3,2-ef][3]benzazapine-2-methanol;

7-chloro-3,4,5,6-tetrahydro-4-methylthieno[4,3,2-ef][3]benzazepine-2-carboxaldehyde;

methyl 7-chloro-3,4,5,6-tetrahydro-4-methylthieno-[4,3,2-ef][3]benzazepine-2-carboxylate;

7-chloro-3,4,5,6-tetrahydro-4-methyl-2-[(2-propenyloxy)methyl]thieno[4,3,2-ef][3]benzazepine;

7-chloro-3,4,5,6-tetrahydro-4-methylthieno-[4,3,2-ef][3]benzazepine;

7-chloro-3,4,5,6-tetrahydro-2,4-dimethyl-thieno[4,3,2-ef][3]benzazepine;

7-chloro-3,4,5,6-tetrahydro-4-methylthieno-[4,3,2-ef][3]benzazepine-2-ethan-2-ol;

7-chloro-3,4,5,6-tetrahydro-4-methylthieno-[4,3,2-ef][3]benzazepine-2-ethan-2-one;

7-chloro-3,4,5,6-tetrahydro-4-methylthieno-[4,3,2-ef][3]benzazepine-2-carboxamide;

N,N-dimethyl-7-chloro-3,4,5,6-tetrahydro-4-methyl-thieno[4,3,2-ef][3]-2-benzazepine-carboxamide;

7-chloro-3,4,5,6-tetrahydro-4-methyl-2-(1-methylethyl)thieno[4,3,2-ef][3]benzazepine;

7-chloro-2-ethyl-3,4,5,6-tetrahydro-4-methyl-thieno[4,3,2-ef][3]benzazepine;

7-chloro-2-propyl-3,4,5,6-tetrahydro-4-methyl-thieno[4,3,2-ef][3]benzazepine; and 2,7-dichloro-3,4,5,6-tetrahydro-4-methyl-thieno[4,3,2-ef][3]benzazepine.

Novel pharmaceutical compositions are obtained when the compounds are incorporated with pharmaceutical carriers into convenient dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds in pharmaceutical dosage units will be an efficacious, nontoxic quantity selected from the range of 0.01–100 mg/kg of active compound, preferably 0.1–50 mg/kg. The selected dose is administered to a human patient in need of treatment from 1–6 times daily, orally, rectally, topically, by inhalation, or injection, or continuously by infusion. Oral administration, however, is preferred because it is more convenient for the patient.

The following examples are illustrative of preparation of Formula (I) compounds. The examples are not intended to limit the scope of the invention as defined hereinabove and as claimed below.

EXAMPLE 1

Method A—Ethyl 7-Chloro-3,4,5,6-tetrahydro-4-methylthieno[4,3,2-ef][3]benzazepine-2-carboxylate (i) 1-[(4-Chlorophenyl)thio]-2-propanone Chloroacetone (32.3 g 0.347 mol) was added to a mixture of 4-chlorothiophenol (50 g. 0.347 mol) and sodium hydroxide (14 g, 0.347 mol) in water (400 ml) and the mixture was stirred at 25° C. for 1 hour. The mixture was extracted with ethyl ether and the organic phase was washed with water, dried with magnesium sulfate and concentrated to give 68 g (98%) of 1-[(4-chlorophenyl)-thio]-2-propanone.

(ii) 5-Chloro-3-methylbenzo[b]thiophene

1-[(4-Chlorophenyl)thio]-2-propanone (50 g, 0.25 mol) was added to polyphosphoric acid (300 g) and the mixture was stirred as the temperature was gradually raised to 120° C. as an exotherm started. The mixture was stirred at 130° C. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo[b]thiophene: bp 120° C. (0.6 mm).

(iii) Ethyl 5-chloro-3-methylbenzo[b]thiophene-2-carboxylate

Butyllithium in hexane (2.6 M, 2.3 ml) was added to a solution of 5-chloro-3-methylbenzo-[b]thiophene (1.0 g, 6 mmol) in ethyl ether (20 ml) stirred at 0° C. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C. for 30 minutes and at 25° C. for 1.5 hours. The mixture was treated with water and the organic phase was dried, concentrated and triturated with hexane to give 1.0 g (67%) of ethyl 5-chloro-3-methylbenzo[b]thiophene-2-carboxylate: mp 92.5°–94° C.

(iv) Ethyl 3-Bromomethyl-5-chlorobenzo[b]-thiophene-2-carboxylate

A mixture of ethyl 5-chloro-3-methyl-benzo[b]thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with a sunlamp for 2 hours. The resulting suspension was cooled, filtered and the filter cake was triturated with methanol to give 9.9 g (85%) of the methanol-insoluble ethyl 3-bromomethyl-5-chlorobenzo-[b]thiophene-2-carboxylate: mp 148°–150° C.

(v) Ethyl 5-Chloro-3-[N-(2,2-dimethoxyethyl)-N-methyl-(aminomethyl)]benzo[b]thiophene-2-carboxylate A mixture of ethyl 3-bromomethyl-5-chlorobenzo[b]-thiophene-2-carboxylate (11.0 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g (96%) of ethyl 5-chloro-3-[N-(2,2-dimethoxyethyl)-N-methyl-(aminomethyl)]benzo[b]thiophene-2-carboxylate.

(vi) Ethyl 7-Chloro-3,4-dihydro-4-methylthieno-[4,3,2-ef][3]benzazepine-2-carboxylate Ethyl 5-chloro-3-[N-(2,2-dimethoxy-ethyl)-N-methyl(aminomethyl)]benzo[b]thiophene-2-carboxylate (3.0 g, 8.1 mmol) was added in portions to trifluoromethanesulfonic acid (10 ml) stirred at 0° C. under argon. The mixture was stirred for 25° C. for 45 minutes and diluted with water. The mixture was basified with aqueous sodium hydroxide and extracted with ethyl ether to give ethyl 7-chloro-3,4-dihydro-4-methylthieno[4,3,2-ef]-[3]benzazepine-2-carboxylate.

(vii) Ethyl 7-Chloro-3,4,5,6-tetrahydro-4-methyl-thieno[4,3,2-ef][3]benzazepine-2-carboxylate Diborane in tetrahydrofuran (1 M, 40 ml) was added to a solution of ethyl 7-chloro-3,4-dihydro-4-methyl-thieno[4,3,2-ef][3]benzazepine-2-carboxylate (2.8 g) in tetrahydrofuran (30 ml) stirred at 0° C. The mixture was refluxed for 3 hours and stirred at 25° C. for 16 hours, cooled, treated with methanol (50 ml), refluxed for 18 hours and concentrated. The residue was triturated with ethyl ether-hexane (3:1) to give 1.6 g (64%) of ethyl 7-chloro-3,4,5,6-tetrahydro-4-methylthieno[4,3,2-ef][3]benzazepine-2-carboxylate: mp 138°–140° C. The free base was treated with hydrogen chloride to give ethyl 7-chloro-3,4,5,6-tetrahydro-4-methylthieno[4,3,2-ef][3]benzazepine-2-carboxylate hydrochloride: mp 240° C.

Method B—Methyl 7-Chloro-3,4,5,6-tetrahydro-4methylthieno[4,3,2-ef][3]benzazepine-2-carboxylate

(i) 3-Bromomethyl-5-chlorobenzo[b]thiophene

Using the general procedure of Example 1, Method A, (iv), replacing ethyl 5-chloro-3-methylbenzo[b]thiophene-2-carboxylate with 5-chloro-3-methylbenzo[b]thiophene gave 2.78 g (57%) of 3-bromomethyl-5-chloro-benzo[b]thiophene: mp 126°–128° C.

(ii) 5-Chloro-3-[N-(2,2-dimethoxyethyl)-N-methyl-(aminomethyl)]benzo[b]thiophene Using the general procedure of Example 1, Method A, (v), replacing ethyl 3-bromomethyl-5-chlorobenzo[b]thiophene-2-carboxylate with 3-bromomethyl-5-chloro-benzo[b]thiophene gave 2.1 g (95%) of 5-chloro-3-[N-(2,2dimethoxyethyl)-N-methyl-(aminomethyl)-]benzo[b]thiophene.

(iii) 5-Chloro-3-[N-(2,2-dimethoxyethyl)-N-methyl-(aminomethyl)]benzo[b]thiophene-2-carboxylic Acid Butyllithium in tetrahydrofuran (2.6 M, 0.04 mol) was added slowly to a solution of 5-chloro-3-[N-(2,2-dimethoxyethyl)-N-methyl(aminomethyl)]benzo[b]-thiophene (10 g, 0.033 mol) in freshly distilled tetrahydrofuran (100 ml) stirred at −30° C. under argon. The mixture was stirred for 30 minutes, treated with dry carbon dioxide for 5 minutes and allowed to warm to 25° C. The mixture was treated with methanol, poured into ice water and extracted with ethyl ether. The aqueous phase was adjusted to pH 7.5 and extracted with methylene chloride. The organic phase was washed with water, dried with magnesium sulfate and concentrated to give 6.0 g (54%) of 5-chloro-3-[N-(2,2-dimethoxyethyl)-N-methyl-(aminomethyl)]benzo[b]thiophene-2-carboxylic acid.

(iv) Methyl 5-Chloro-3-[N-(2,2-dimethoxyethyl)-N-methyl-(aminomethyl)]benzo[b]thiophene-2-carboxylate A suspension of 5-chloro-3-[N-(2,2-dimethoxyethyl)-N-methyl(aminomethyl)]benzo[b]thiophene-2-carboxylic acid (5.0 g, 14.5 mmol) in methylene chloride-tetrahydrofuran was stirred at 0° C. and treated with excess diazomethane in ethyl ether. The mixture was stirred for 2 hours at 0° C., treated with a stream of argon and concentrated to give 5.0 g (96%) of methyl 5-chloro-3-[N-(2,2-dimethoxyethyl)-N-methyl-(amihomethyl)]benzo[b]-thiophene-2-carboxylate.

(v) Methyl 7-Chloro-3,4-dihydro-4-methylthieno-[4,3,2-ef][3]benzazepine-2-carboxylate Using the general procedure of Example 1, Method A, (vi), replacing ethyl 5-chloro-3-[N-(2,2-dimethoxyethyl)-N-methyl(aminomethyl)]benzo[b]thiophene-2-carboxylate with methyl 5-chloro-3-[N-(2,2-dimethoxyethyl)-N-methyl(aminomethyl)]benzo[b]thiophene-2-carboxylate gave methyl 7-chloro-3,4-dihydro-4-methylthieno[4,3,2-ef]-[3]benzazepine-2-carboxylate.

(vi) Methyl 7-Chloro-3,4,5,6-tetrahydro-4-methylthieno[4,3,2-ef][3]benzazepine-2-carboxylate A solution of methyl 7-chloro-3,4-dihydro-4-methyl-thieno[4,3,2-ef][3]benzazepine-2-carboxylate in ethanol (30 ml) containing platinum oxide (0.3 g) was shaken under hydrogen (30 psi) for 2 hours. The mixture was filtered, concentrated and treated with ethereal hydrogen chloride to give methyl 7-chloro 3,4,5,6-tetrahydro-4-methylthieno[4,3,2-ef][3]benzazepine-2-carboxylate hydrochloride: mp 215°–216° C.

EXAMPLE 2

7-Chloro-3,4,5,6-tetrahydro-4-methylthieno-[4,3,2-ef][3]benzazepine-2-methanol A solution of methyl 7-chloro-3,4,5,6-tetrahydro-4-methylthieno[4,3,2-ef][3]benzazepine-2-carboxylate (4.0 g, 13.5 mmol), prepared as in Example 1, in ethyl ether (48 ml) was treated with lithium aluminum hydride (0.53 g, 14 mmol). The mixture was stirred for 1.5 hours, cooled and treated carefully with water (2.0 ml), 10% sodium hydroxide (1.0 ml) and water (2.0 ml). The resulting mixture was filtered and the solvent evaporated to give 2.1 g (57%) of 7-chloro-3,4,5,6-tetrahydro-4-methylthieno-[4,3,2-ef][3]benzazepine-2-methanol: mp 184°–185° C.

EXAMPLE 3

7-Chloro-3,4,5,6-tetrahydro-4-methylthieno[4,3,2-ef][3]benzazepine-2-carboxaldehyde A solution of 7-chloro-3,4,5,6-tetrahydro-4-methyl-thieno[4,3,2-ef][3]benzazepine-2-methanol, prepared as in Example 2, (1.6 g, 6 mmol) in dichloromethane (150 ml) was stirred under argon with activated manganese dioxide (8.3 g) for 2 hours. The mixture was filtered through an acid washed silicon dioxide filtration agent (Celite ®) and the filtrate was dried with magnesium sulfate and concentrated to give a 63% yield of 7-chloro-3,4,5,6-tetrahydro-4-methylthieno[4,3,2-ef][3]-benzazepine-2-carboxaldehyde.

EXAMPLE 4

7-Chloro-3,4,5,6-tetrahydro-4-methylthieno-[4,3,2-ef][3]benzazepine-2-carboxylic Acid A mixture of ethyl 7-chloro-3,4,5,6-tetrahydro-4-methylthieno[4,3,2-ef][3]benzazepine-2-carboxylate, prepared as in Example 1, (30 g), 6N hydrochloric acid (300 ml) and acetic acid (300 ml) was heated to reflux for 3 hours, cooled and filtered to give 15 g of 7-chloro-4,5,6-tetrahydro-4-methylthieno[4,3,2-ef][3]benzazepine-2-carboxylic acid hydrochloride. The filtrate was concentrated in vacuo and filtered to give an additional 13 g of product.

EXAMPLE 5 t-Butyl 7-Chloro-3,4,5,6-tetrahydro-4-methylthieno[4,3,2-ef][3]benzazepine-2-carboxylate A mixture of ethyl 7-chloro-3,4,5,6-tetrahydro-4-methylthieno[4,3,2-ef][3]benzazepine-2-carboxylate, prepared as in Example 1, 5A molecular sieves, t-butanol and dry toluene is treated with potassium t-butoxide and stirred at 80° C. to give t-butyl 7-chloro-3,4,5,6-tetrahydro-4-methylthieno[4,3,2-ef][3]benzazepine-2-carboxylate.

EXAMPLE 6

7-Chloro-3,4,5,6-tetrahydro-4-methylthieno[4,3,2-ef][3]-benzazepine-2-carbonyl Chloride and 2-Propenyl 7-Chloro-3,4,5,6-tetrahydro-4-methylthieno-[4,3,2-ef][3]benzazepine-2-carboxylate A mixture of 7-chloro-3,4,5,6-tetrahydro-4-methylthieno[4,3,2-ef][3]benzazepine-2-carboxylic acid hydrochloride, prepared as in Example 4, (28 g) and thionyl chloride (100 ml) in toluene (50 ml) was heated to reflux for 5 hours, cooled and concentrated in vacuo. The residue was treated with toluene, concentrated in vacuo and the residue was stirred with ethyl ether and filtered to give 7-chloro-3,4,5,6-tetrahydro-4-methyl-thieno[4,3,2-ef][3]benzazepine-2-carbonyl chloride hydrochloride: mp 27° C.

A suspension of 7-chloro-3,4,5,6-tetrahydro-4-methylthieno[4,3,2-ef][3]benzazepine-2-carbonyl chloride hydrochloride in tetrahydrofuran is stirred and treated with allyl alcohol and triethylamine to give 2-propenyl 7-chloro-3,4,5,6-tetrahydro-4-methyl-thieno[4,3,2-ef][3]-benzazepine-2-carboxylate hydrochloride.

EXAMPLE 7

7-Chloro-3,4,5,6-tetrahydro-N,N,4-trimethylthieno-[4,3,2-ef][3]benzazepine-2-carboxamide Dimethylamine was bubbled through a mixture of 7-chloro-3,4,5,6-tetrahydro-4-methylthieno[4,3,2-ef][3]benzazepine-2-carbonyl chloride hydrochlorid, prepared as in Example 6, (0.5 g) in tetrahydrofuran (30 ml) stirred at −20° C. for 5 minutes. The mixture was stirred and allowed to warm to 25° C. for 2 hours, concentrated in vacuo, diluted with water and extracted with methylene chloride. The organic phase was dried with magnesium sulfate and concentrated in vacuo to give an oil which was chromatographed on silica gel eluted with methanol-methylene chloride (1:10) to give 125 mg of 7-chloro-N,N-dimethyl-3,4,5,6-tetrahydro-4-methylthieno[4,3,2-ef][3]benzazepine-2-carboxamide: mp 103°-105° C.

EXAMPLE 8

7-Chloro-3,4,5,6-tetrahydro-α,α,4-trimethylthieno-[4,3,2-ef][3]benzazepine-2-acetonitrile A solution of 7-chloro-3,4,5,6-tetrahydro-4-methyl-thieno[4,3,2-ef][3]benzazepine-2-methanol (0.01 mole), prepared as in Example 2, in thionyl chloride (30 ml) was heated to reflux under argon, cooled and concentrated to give 7-chloro-2-chloromethyl-3,4,5,6-tetrahydro-4-methylthieno[4,3,2-ef][3]benzazepine hydrochloride.

A mixture of 7-chloro-2-chloromethyl-3,4,5,6-tetrahydro-4-methylthieno[4,3,2-ef][3]benzazepine (5.0 mmol), potassium cyanide (10 mmol) and 18-crown-6 (0.1 mmol) in dry acetonitrile (25 ml) is stirred vigorously at room temperature. The reaction mixture is filtered and concentrated to one-third its volume, basified with 5% sodium bicarbonate and extracted with methylene chloride. The organic phase is dried and concentrated to give 7-chloro-3,4,5,6-tetrahydro-4-methylthieno[4,3,2-ef][3]benzazepine-2-acetonitrile.

A solution of 7-chloro-3,4,5,6-tetrahydro-4-methyl-thieno[4,3,2-ef][3]benzazepine-2-acetonitrile (3.0 mmol) in anhydrous tetrahydrofuran (25 ml) at −78° is treated with lithium diisopropylamide (6.0 mmol). The mixture is stirred and treated with a solution of methyl iodide (6.0 mmol) in dry tetrahydrofuran (5 ml) added dropwise. The reaction mixture is stirred, quenched with water and concentrated. The resulting residue is extracted with ether and the organic phase is dried and concentrated to give 7-chloro-3,4,5,6-tetrahydro-α,α,4-trimethylthieno[4,3,2-ef][3]benzazepine-2-acetonitrile.

EXAMPLE 9

7-Chloro-3,4,5,6-tetrahydro-4-methylthieno[4,3,2-ef][3]benzazepine-2-carboxaldehyde Oxime and 7-Chloro-3,4,5,6-tetrahydro-4-methylthieno[4,3,2-ef][3]benzazepine-2-carbonitrile 7-Chloro-3,4,5,6-tetrahydro-4-methylthieno[4,3,2-ef][3]benzazepine-2-carboxaldehyde, prepared as in Example 3, is added to a solution of hydroxylamine hydrochloride to give 7-chloro-3,4,5,6-tetrahydro-4-methyl-thieno-[4,3,2-ef][3]benzazepine-2-carboxaldehyde oxime hydro-chloride.

A mixture of 7-chloro-3,4,5,6-tetrahydro-4-methyl-thieno[4,3,2-ef][3]benzazepine-2-carboxaldehyde oxime hydrochloride and triethylamine in methylene chloride is stirred and cooled to −78° C. and treated with a solution of trifluoromethanesulfonic anhydride in methylene chloride to give 7-chloro-3,4,5,6-tetrahydro-4-methylthieno[4,3,2-ef][3]benzazepine-2-carbonitrile.

EXAMPLE 10

2-Acetyl-7-chloro-3,4,5,6-tetrahydro-4-methylthieno-[4,3,2-ef][3]benzazepine Methylmagnesium bromide in tetrahydrofuran (3M, 15 ml, 45 mmol) was added to a solution of ethyl 7-chloro-3,4,5,6-tetrahydro-4-methylthieno[4,3,2-ef][3]benzazepine-2-carboxylate, prepared as in Example 1, Method A, (3.09 g, 10 mmol) in ethyl ether (100 ml) stirred under argon. The mixture was stirred for 1 hour, treated with saturated aqueous ammonium chloride and extracted with ethyl ether. The organic phase was dried with magnesium sulfate and concentrated in vacuo to give a residue which was chromatographed on silica gel eluted with methanol-methylene chloride (1:10) to give 2-acetyl-7-chloro-3,4,5,6-tetrahydro-4-methylthieno[4,3,2-ef][3]benzazepine: mp 78°-80° C.

EXAMPLE 11

7-Chloro-3,4,5,6-tetrahydro-4-methylthieno-4,3,2-ef][3]benzazepine

A solution of ethyl 7-chloro-3,4,5,6-tetrahydro-4-methylthieno[4,3,2-ef][3]benzazepine-2-carboxylate, prepared as in Example 1, (5.0 g, 16 mmol) in 1,2-dichloroethane (80 ml) was treated with ethyl chloroformate (0.3 g, 80 mmol) and heated to reflux for 7 hours. The mixture was concentrated in vacuo and the residue recrystallized from ethanol to give 3 g of ethyl 7-chloro-4-ethoxycarbonyl-3,4,5,6-tetrahydrothieno[4,3,2-ef][3]benzazepine-2-carboxylate.

Ethyl 7-chloro-4-ethoxycarbonyl-3,4,5,6-tetrahydrothieno[4,3,2-ef][3]benzazepine-2-carboxylate (3.0 g) in acetic acid (80 ml) and 6N hydrochloric acid (40 ml) was heated to reflux for 10 hours, cooled and filtered to give 1.8 g of 7-chloro-4-ethoxycarbonyl-3,4,5,6-tetrahydrothieno[4,3,2-ef][3]benzazepine-2-carboxylic acid.

A mixture of 7-chloro-4-ethoxycarbonyl-3,4,5,6-tetrahydrothieno[4,3,2-ef][3]benzazepine-2-carboxylic acid (0.6 g) and activated copper Powder (1.0 g) in quinoline (10 ml) was heated to 200° C. for 30 minutes to give 7-chloro-4-ethoxycarbonyl-3,4,5,6-tetrahydrothieno[4,3,2-ef]-[3]benzazepine.

A solution of 7-chloro-4-ethoxycarbonyl-3,4,5,6-tetrahydrothieno[4,3,2-ef][3]benzazepine (0.5 g, 1.7 mmol) in ethyl ether (25 ml) was treated with lithium aluminum hydride (78 mg, 2 mmol) and stirred for 1.5 hours. The mixture was treated with water (2 drops), 10% aqueous sodium hydroxide (4 drops) and water (8 drops), filtered and the filtrate was concentrated in vacuo. The residue was treated with ethereal hydrogen bromide to give 0.34 g (xx%) of 7-chloro-3,4,5,6-tetrahydro-4-methylthieno[4,3,2-ef][3]benzazepine hydrobromide: mp 248° C.

Alternatively, 7-chloro-3,4,5,6-tetrahydro-4-methylthieno[4,3,2-ef][3]benzazepine-2-carboxylic acid hydrochloride, prepared as in Example 4, (3.0 g) was heated to 285° C. for 5 minutes, cooled and the residue partitioned between ethyl ether and water. The organic phase was dried with magnesium sulfate and concentrated in vacuo to give 7-chloro-3,4,5,6-tetrahydro-4-methylthieno[4,3,2-ef][3]benzazepine.

EXAMPLE 12

7-Chloro-3,4,5,6-tetrahydro-2,4-dimethylthieno-[4,3,2-ef][3]benzazepine

A solution of 7-chloro-3,4,5,6-tetrahydro-4-methylthieno[4,3,2-ef][3]benzazepine-2-methanol hydrochloride, prepared as in Example 2, (0.2 g) in ethanol (30 ml) was treated with concentrated hydrochloric acid (5 drops) and platinum oxide (160 mg) and was shaken under hydrogen for 6 hours. The mixture was filtered, concentrated in vacuo, basified and extracted with ethyl ether. The organic phase was concentrated in vacuo and the residue was chromatographed on a preparative silica gel plate eluted with methanol methylene chloride (1:10) to give an oil. The oil was dissolved in ethyl ether and treated with ethereal hydrogen chloride to give 7-chloro-3,4,5,6-tetrahydro-2,4-dimethylthieno[4,3,2-ef][3]benzazepine hydrochloride: mp 252° C.

EXAMPLE 13

7-Chloro-2-ethyl-3,4,5,6-tetrahydro-4-methylthieno[4,3,2-ef][3]benzazepine

Using the general procedure of Example 12, replacing 7-chloro-3,4,5,6-tetrahydro-4-methylthieno[4,3,2-ef][3]benzazepine-2-methanol hydrochloride with 7-chloro-2-ethenyl-3,4,5,6-tetrahydro-4-methylthieno[4,3,2-ef][3]benzazepine hydrochloride gave 7-chloro-2-ethyl-3,4,5,6-tetrahydro-4-methylthieno[4,3,2-ef][3]benzazepine hydrochloride: mp 195° C.

EXAMPLE 14

7-Chloro-3,4,5,6-tetrahydro-4-methyl-2-(2-methylpropyl)thieno[4,3,2-ef][3]benzazepine A solution of butyllithium in hexane is added to a suspension of isopropyltriphenylphosphonium iodide in freshly distilled tetrahydrofuran stirred under argon at −15° C. The mixture is stirred at −10° C. to −15° C. for 20 minutes and treated with a solution of 7-chloro-3,4,5,6-tetrahydro-4-methylthieno[4,3,2-ef][3]benzazepine-2-carbox-aldehyde, prepared as in Example 3, in tetrahydrofuran added dropwise to give 7-chloro-3,4,5,6-tetrahydro-4-methyl-2-(2-methyl-1-propenyl)-thieno[4,3,2-ef][3]benzazepine.

Using the procedure of Example 12, replacing 7-chloro-3,4,5,6-tetrahydro-4-methylthieno[4,3,2-ef][3]-benzazepine-2-methanol hydrochloride with 7-chloro-3,4,5,6-tetrahydro-4-methyl-2-(2-methyl-1-propenyl)-thieno-[4,3,2-ef][3]benzazepine hydrochloride gives 7-chloro-3,4,5,6-tetrahydro-4-methyl-2-(2-methylpropyl)thieno[4,3,2-ef][3]benzazepine hydrochloride.

EXAMPLE 15

Ethyl 7-Chloro-3,4,5,6-tetrahydro-4-methylthieno-[4,3,2-ef][3]benzazepine-2-propanoate A 50% dispersion of sodium hydride in mineral oil (58 mg, 1.2 mmol) was added to a stirred solution of triethyl phosphonoacetate (268 mg, 1.2 mmol) in ethyl ether (30 ml) and stirred for 15 minutes. The mixture was treated with a solution of 7-chloro-3,4,5,6-tetrahydro-4-methylthieno[4,3,2-ef][3]benzazepine-2-carbox-aldehyde, prepared as in Example 3, (300 mg, 1.4 mmol) in ethyl ether (30 ml), stirred at 25° C. for 16 hours, quenched with water and extracted with ethyl ether. The organic phase was washed, dried and concentrated and the residue was treated with ethereal hydrogen chloride to give 230 mg (40%) of ethyl (E)-3-(7-chloro-3,4,5,6-tetrahydro-4-methylthieno[4,3,2-ef][3]benzazepin-2-yl)-2-propenoate hydrochloride: mp 234°–236° C.

Using the general procedure of Example 12, replacing 7-chloro-3,4,5,6-tetrahydro-4-methylthieno[4,3,2-ef][3]benzazepine-2-methanol hydrochloride with ethyl (E)-3-(7-chloro-3,4,5,6-tetrahydro-4-methylthieno-[4,3,2-ef][3]benzazepin-2-yl)-2-propenoate hydrochloride gives ethyl 7-chloro-3,4,5,6-tetrahydro-4-methylthieno-[4,3,2-ef][3]benzazepine-2-propanoate hydrochloride.

EXAMPLE 16

7-Chloro-3,4,5,6-tetrahydro-4-methylthieno[4,3,2-ef][3]benzazepine-2-propanol

Using the general procedure of Example 2, replacing ethyl 7-chloro-3,4,5,6-tetrahydro-4-methylthieno-[4,3,2-ef][3]benzazepine-2-carboxylate with ethyl 7-chloro-3,4,5,6-tetrahydro-4-methylthieno[4,3,2-ef][3]benzazepine-2-propanoate, prepared as in Example 15, gives 7-chloro-3,4,5,6-tetrahydro-4-methylthieno[4,3,2-ef][3]-benzazepine-2-propanol.

EXAMPLE 17

7-Chloro-2-(3-chloropropyl)-3,4,5,6-tetrahydro-4-methylthieno[4,3,2-ef][3]benzazepine and 7-Chloro-3,4,5,6-tetrahydro-4-methyl-2-(2-propenyl)-thieno[4,3,2-ef][3]benzazepine 7-Chloro-3,4,5,6-tetrahydro-4-methylthieno-[4,3,2-ef][3]benzazepine-2-propanol hydrochloride, prepared as in Example 16, is treated with thionyl chloride and triethylamine in chloroform to give 7-chloro-2-(3-chloropropyl)-3,4,5,6-tetrahydro-4-methylthieno[4,3,2-ef][3]benzazepine hydrochloride.

7-Chloro-2-(3-chloropropyl)-3,4,5,6-tetrahydro-4-methylthieno[4,3,2-ef][3]benzazepine is converted to the free base and treated with lithium diiscprcpylamide in tetrahydrofuran to give 7-chloro-3,4,5,6-tetrahydro-4-methyl-2-(2-propenyl)thieno[4,3,2-ef][3]benzazepine.

EXAMPLE 18

7-Chloro-3,4,5,6-tetrahydro-α,α,4-trimethylthieno-[4,3,2-ef][3]benzazepine-2-butanenitrile Using the general procedure of Example 8, replacing 7-chloro-3,4,5,6-tetrahydro-4-methylthieno[4,3,2-ef][3]benzazepine-2-methanol with 7-chloro-3,4,5,6-tetrahydro-4-methylthieno[4,3,2-ef][3]benzazepine-2-propanol, prepared as in Example 16, gives 7-chloro-3,4,5,6-tetrahydro-α,α,4-trimethylthieno-4,3,2-ef][3]benzazepine-2-butanenitrile.

EXAMPLE 19

7-Chloro-3,4,5,6-tetrahydro-4-methyl-2-[(2-propenyloxy)methyl]thieno[4,3,2-ef][3]benzazepine A solution of 7-chloro-3,4,5,6-tetrahydro-4-methyl-thieno[4,3,2-ef][3]benzazepine-2-methanol, prepared as in Example 2, (0.2 g, 0.75 mmol) in dimethylformamide (20 ml) was treated with a 50% dispersion of sodium hydride (37 mg, 0.78 mmol), stirred for 15 minutes, treated with allyl iodide (126 mg, 0.75 mmol) and stirred for 18 hours. The usual workup gave an oil which was dissolved in ethyl ether and treated with hydrogen chloride to give 0.15 g (58%) of 7-chloro-3,4,5,6-tetrahydro-4-methyl-2-[(2-propenyloxy)methyl]-thieno[4,3,2-ef][3]benzazepine hydrochloride: mp 140°-142° C.

EXAMPLE 20

7-Chloro-3,4,5,6-tetrahydro-4-methyl-2-[(propyloxy)-methyl]thieno[4,3,2-ef][3]benzazepine Using the general procedure of Example 12, replacing 7-chloro-3,4,5,6-tetrahydro-4-methylthieno-[4,3,2-ef][3]benzazepine-2-methanol hydrochloride with 7-chloro-3,4,5,6-tetrahydro-4-methyl-2-[(2-propenyloxy)methyl]thieno[4,3,2-ef][3]benzazepine hydrochloride, prepared as in Example 19, gives 7-chloro-3,4,5,6-tetrahydro-4-methyl-2-[(propyloxy)methyl]thieno[4,3,2-ef]-[3]benzazepine hydrochloride.

EXAMPLE 21

7-Chloro-3,4,5,6-tetrahydro-4-methyl-2-[(3-methyl-2-butenyloxy)methyl]thieno[4,3,2-ef][3]benzazepine Using the procedure of Example 19, replacing allyl iodide with 3-methyl-2-butenyl bromide, gives 7-chloro-3,4,5,6-tetrahydro-4-methyl-2-[(3-methyl-2-butenyloxy)methyl]thieno[4,3,2-ef][3]benzazepine hydrochloride.

EXAMPLE 22

7-Chloro-3,4,5,6-tetrahydro-4-methyl-2-[(2-propenyl-thio)methyl]thieno[4,3,2-ef][3]benzazepine A solution of ethyl 7-chloro-4-ethoxycarbonyl-3,4,5,6-tetrahydrothieno[4,3,2-ef][3]benzazepine-2-carboxylate, prepared as in Example 11, in tetrahydrofuran is stirred under argon and treated with 2 M lithium borohydride in tetrahydrofuran followed by trimethyl borate to give 7-chloro-4-ethoxycarbonyl-3,4,5,6-tetrahydrothieno[4,3,2-ef][3]benzazepine-2-methanol.

A solution of 7-chloro-4-ethoxycarbonyl-3,4,5,6-tetrahydrothieno[4,3,2-ef][3]benzazepine-2-methanol and carbon tetrabromide in methylene chloride is stirred at 0° C. and treated with triphenylphosphine. The mixture is stirred for 20 minutes at 0° C., concentrated and the residue chromatographed on silica gel eluted with chloroform to give 2-bromomethyl-7-chloro-4-ethoxycarbonyl-3,4,5,6-tetrahydrothieno[4,3,2-ef]-[3]benzazepine.

Using the general procedure of Example 19, replacing 7-chloro-3,4,5,6-tetrahydro-4-methylthieno-[4,3,2-ef][3]benzazepine-2-methanol with allyl mercaptan and allyl iodide with 2-bromcmethyl-7-chloro-4-ethoxycarbonyl-3,4,5,6-tetrahydrothieno[4,3,2-ef][3]benzazepine gives 7-chloro-4-ethoxycarbonyl-3,4,5,6-tetrahydro-2-[(2-propenylthio)methyl]thieno[4,3,2-ef][3]benzazepine.

Using the general procedure of Example 11, replacing 7-chloro-4-ethoxycarbonyl-3,4,5,6-tetrahydrothieno[4,3,2-ef][3]benzazepine with 7-chloro-4-ethoxycarbonyl-3,4,5,6-tetrahydro-2-[(2-propenylthio)methyl]-thieno-[4,3,2-ef][3]benzazepine gives 7-chloro-3,4,5,6-tetrahydro-4-methyl-2-[(2-propenylthio)methyl]thieno[4,3,2-ef][3]benzazepine.

EXAMPLE 23

2-Bromo-7-chloro-3,4,5,6-tetrahydro-4-methylthieno-[4,3,2-ef][3]benzazepine

A solution of 7-chloro-3,4,5,6-tetrahydro-4-methyl-thieno[4,3,2-ef][3]benzazepine, prepared as in Example 11, in acetic acid is treated with hydrogen bromide and then with bromine to give 2-bromo-7-chloro-3,4,5,6-tetrahydro-4-methylthieno[4,3,2-ef][3]benzazepine hydrobromide.

EXAMPLE 24

7-Chloro-3,4,5,6-tetrahydro-4-methyl-2-(trifluoromethyl)thieno[4,3,2-ef][3]benzazepine A solution of 7-chloro-4-ethoxycarbonyl-3,4,5,6-tetrahydrothieno[4,3,2-ef][3]benzazepine, prepared as in Example 11, in acetic acid is treated with a solution of bromine in acetic acid to give 2-bromo-7-chloro-4-ethoxycarbonyl-3,4,5,6-tetrahydrothieno[4,3,2-ef][3]benzazepine.

A mixture of 2-bromo-7-chloro-4-ethoxycarbonyl-3,4,5,6-tetrahydrothieno[4,3,2-ef][3]benzazepine, trifluoromethyl iodide and activated copper in dimethylformamide is heated in a stainless steel pressure vessel to 150° C. for 48–72 hours. The mixture is cooled, diluted with water and ethyl acetate, filtered through an acid washed silicon dioxide filtration agent (Celite ®) and the organic phase is washed with water and brine, dried with sodium sulfate and concentrated. The residue is chromatographed on silica gel to give 7-chloro-4-ethoxycarbonyl-3,4,5,6-tetrahydro-2-(trifluoromethyl)thieno-[4,3,2-ef][3]benzazepine.

Using the general procedure of Example 11, 7-chloro-4-ethoxycarbonyl-3,4,5,6-tetrahydrothieno-[4,3,2-ef][3]benzazepine is replaced with 7-chloro-4-ethoxycarbonyl-3,4,5,6-tetrahydro-2-(trifluoromethyl)-thieno[4,3,2-ef][3]benzazepine to give 7-chloro-3,4,5,6-tetrahydro-4-methyl-2-(trifluoromethyl)thieno[4,3,2-ef][3]benzazepine.

EXAMPLE 25

7-Chloro-3,4,5,6-tetrahydro-4-methyl-2-nitro-thieno[4,3,2-ef][3]benzazepine

Using the general procedure of Example 23, replacing bromine with nitric acid gives 7-chloro-3,4,5,6-tetrahydro-4-methyl-2-nitrothieno[4,3,2-ef][3]benzazepine.

EXAMPLE 26

Ethyl 7-Chloro-3,4,5,6-tetrahydrothieno-[4,3,2-ef][3]benzazepine-2-carboxylate

A mixture of ethyl 7-chloro-3,4,5,6-tetrahydro-4-methylthieno[4,3,2-ef][3]benzazepine-2-carboxylate, prepared as in Example 1, (4.5 g, 14.5 mmol), trichloroethyl chloroformate (12.7 g, 58 mmol) and potassium carbonate (1.0 g) in toluene (100 ml) was heated to reflux for 72 hours, cooled and filtered. The filtrate was concentrated in vacuo, let stand and filtered to give 2.1 g of ethyl 7-chloro-3,4 5,6-tetrahydro-2-(trichloroethoxycarbonyl)thieno[4,3,2-ef][3]benzazepine-2-carboxylate.

A mixture of ethyl 7-chloro-3,4,5,6-tetrahydro-2-(trichloroethoxycarbonyl)thieno[4,3,2-ef][3]benzazepine-2-carboxylate (2.1 g) and zinc powder (4.5 g) in acetic acid was stirred for 72 hours, filtered and the filtrate was diluted with water, basified with 50% aqueous sodium hydroxide and extracted with ethyl ether. The organic phase was dried with magnesium sulfate and concentrated in vacuo to give 0.84 g of ethyl 7-chloro-3,4,5,6-tetrahydrothieno[4,3,2-ef][3]benzazepine-2-carboxylate.

EXAMPLE 27

7-Chloro-4-ethyl-3,4,5,6-tetrahydrothieno-[4,3,2-ef][3]benzazepine-2-methanol

A solution of ethyl 7-chloro-3,4,5,6-tetrahydrothieno[4,3,2-ef][3]benzazepine-2-carboxylate, prepared as in Example 26, and triethylamine in dry tetrahydrofuran is stirred and treated with acetyl chloride to give ethyl 4-acetyl-7-chloro-3,4,5,6-tetrahydrothieno[4,3,2-ef][3]-benzazepine-2-carboxylate.

A solution of ethyl 4-acetyl-7-chloro-3,4,5,6-tetrahydrothieno[4,3,2-ef][3]benzazepine-2-carboxylate in tetrahydrofuran is added dropwise to a stirred suspension of lithium aluminum hydride in ethyl ether to give 7-chloro-4-ethyl-3,4,5,6-tetrahydrothieno[4,3,2-ef][3]-benzazepine-2-methanol.

EXAMPLE 28

7-Chloro-4-ethyl-3,4,5,6-tetrahydrothieno-[4,3,2-ef][3]benzazepine-2-carboxaldehyde Using the general procedure of Example 3, replacing 7-chloro-3,4,5,6-tetrahydro-4-methylthieno-[4,3,2-ef][3]benzazepine-2-methanol with 7-chloro-4-ethyl-3,4,5,6-tetrahydrothieno[4,3,2-ef][3]benzazepine-2-methanol, prepared as in Example 27, gives 7-chloro-4-ethyl-3,4,5,6-tetrahydrothieno[4,3,2-ef][3]benzazepine-2-carboxaldehyde.

EXAMPLE 29

7-Chloro-3,4,5,6-tetrahydro-2-methylthieno[4,3,2-ef][3]-benzazepine and 7-Chloro-3,4,5,6-tetrahydro-2-methyl-4-(2-propenyl)-thieno[4,3,2-ef][3]benzazepine Using the general procedure of Example 26, replacing ethyl 7-chloro-3,4,5,6-tetrahydro-4-methyl-thieno[4,3,2-ef][3]benzazepine-2-carboxylate with 7-chloro-3,4,5,6-tetrahydro-2,4-dimethylthieno-[4,3,2-ef][3]benzazepine, prepared as in Example 12, gives 7-chloro-3,4,5,6-tetrahydro-2-methylthieno[4,3,2-ef][3]benzazepine.

A solution of 7-chloro-3,4,5,6-tetrahydro-2-methylthieno[4,3,2-ef][3]benzazepine in dry acetone is treated with potassium carbonate and allyl iodide to give 7-chloro-3,4,5,6-tetrahydro-2-methyl-4-(2-propenyl)-thieno-[4,3,2-ef][3]benzazepine.

EXAMPLE 30

Ethyl 3,4,5,6-Tetrahydro-4-methylthieno[4,3,2-ef][3]benzazepine-2-carboxylate

A mixture of ethyl 7-chloro-3,4,5,6-tetrahydro-4-methylthieno[4,3,2-ef][3]benzazepine-2-carboxylate hydrochloride, prepared as in Example 1, and platinum oxide in absolute ethanol is shaken under hydrogen to give ethyl 3,4,5,6-tetrahydro-4-methylthieno[4,3,2-ef][3]-benzazepine-2-carboxylate hydrochloride.

EXAMPLE 31

Ethyl 3,4,5,6-Tetrahydro-4-methyl-7-nitrothieno[4,3,2-ef][3]benzazepine-2-carboxylate A solution of ethyl 3,4,5,6-tetrahydro-4-methyl-thieno[4,3,2-ef][3]benzazepine-2-carboxylate hydrochloride, prepared as in Example 30, in sulfuric acid is stirred at 0° C. and treated with 70% nitric acid to give ethyl 3,4,5,6-tetrahydro-4-methyl-7-nitrothieno[4,3,2-ef]benzazepine-2-carboxylate.

EXAMPLE 32

Ethyl 7-Amino-3,4,5,6-tetrahydro-4-methylthieno-[4,3,2-ef][3]benzazepine-2-carboxylate Using the general procedure of Example 12, replacing 7-chloro-3,4,5,6-tetrahydro-4-methylthieno-[4,3,2,ef][3]benzazepine-2-methanol hydrochloride with ethyl 3,4,5,6-tetrahydro-4-methyl-7-nitrothieno[4,3,2-ef][3]benzazepine-2-carboxylate, prepared as in Example 31, gives ethyl 7-amino-3,4,5,6-tetrahydro-4-methyl-thieno-[4,3,2-ef][3]benzazepihe-2-carboxylate.

EXAMPLE 33

Ethyl 7-Dimethylamino-3,4,5,6-tetrahydro-4-methylthieno-[4,3,2-ef][3]benzazepine-2-carboxylate A mixture of ethyl 3,4,5,6-tetrahydro-4-methyl-7-nitrothieno[4,3,2-ef][3]benzazepine-2-carboxylate, prepared as in Example 31, 37% formalin and platinum oxide in absolute ethanol is shaken under hydrogen to give ethyl 7-dimethylamino-3,4,5,6-tetrahydro-4-methylthieno[4,3,2-ef]-[3]benzazepine-2-carboxylate.

EXAMPLE 34

Ethyl
7-Fluoro-3,4,5,6-tetrahydro-4-methylthieno-[4,3,2-ef][3]benzazepine-2-carboxylate,
7-Fluoro-3,4,5,6-tetrahydro-4-methylthieno-[4,3,2-ef][3]benzazepine-2-methanol, and
7-Fluoro-3,4,5,6-tetrahydro-4-methylthieno-[4,3,2-ef][3]benzazepine-2-carboxaldehyde Using the general procedure of Example 1, replacing 4-chlorothiophenol with 4-fluorothiophenol gives ethyl 7-fluoro-3,4,5,6-tetrahydro-4-methylthieno[4,3,2-ef]-[3]benzazepine-2-carboxylate.

Using the general procedure of Example 2, replacing ethyl 7-chloro-3,4,5,6-tetrahydro-4-methylthieno[4,3,2-ef][3]benzazepine-2-carboxylate with ethyl 7-fluoro-3,4,5,6-tetrahydro-4-methylthieno-[4,3,2-ef][3]benzazepine-2-carboxylate gives 7-fluoro-3,4,5,6-tetrahydro-4-methylthieno[4,3,2-ef][3]benzazepine-2-methanol.

Using the general procedure of Example 3, replacing 7-chloro-3,4,5,6-tetrahydro-4-methylthieno-[4,3,2-ef][3]benzazepine-2-methanol with 7-fluoro-3,4,5,6-tetrahydro-4-methylthieno[4,3,2-ef][3]benzazepine-2-methanol gives 7-fluoro-3,4,5,6-tetrahydro-4-methyl-thieno-[4,3,2-ef][3]benzazepine-2-carboxaldehyde.

EXAMPLE 35

3,4,5,6-Tetrahydro-4-methylthieno[4,3,2-ef][3]-benzazepine-2-methanol

Using the general procedure of Example 2, replacing ethyl 7-chloro-3,4,5,6-tetrahydro-4-methylthieno[4,3,2-ef][3]benzazepine-2-carboxylate with ethyl 3,4,5,6-tetrahydro-4-methylthieno[4,3,2-ef][3]benzazepine-2-carboxylate, prepared as in Example 30, gives 3,4,5,6-tetrahydro-4-methylthieno[4,3,2-ef][3]benzazepine-2-methanol hydrochloride.

EXAMPLE 36

Ethyl
7-Bromo-3,4,5,6-tetrahydro-4-methylthieno[4,3,2-ef][3]benzazepine-2-carboxylate Using the general procedure of Example 1, replacing 4-chlorothiophenol with 4-bromothiophenol gives ethyl 7-bromo-3,4,5,6-tetrahydro-4-methylthieno[4,3,2-ef]-[3]benzazepine-2-carboxylate.

EXAMPLE 37

Ethyl
7,9-Dichloro-3,4,5,6-tetrahydro-4-methylthieno-[4,3,2-ef][3]benzazepine-2-carboxylate Using the general procedure of Example 1, replacing 4-chlorothiophenol with 2,4-dichlorothiophenol yields ethyl 7,9-dichloro-3,4,5,6-tetrahydro-4-methyl-thieno[4,3,2-ef][3]benzazepine-2-carboxylate hydrochloride.

EXAMPLE 38

Ethyl
7-Cyano-3,4,5,6-tetrahydro-4-methylthieno[4,3,2-ef][3]benzazepine-2-carboxylate,
7-Cyano-3,4,5,6-tetrahydro-4-merhylthieno[4,3,2-ef][3]benzazepine-2-methanol, and
7-Cyano-3,4,5,6-tetrahydro-4-methylthieno[4,3,2-ef][3]benzazepine-2-carboxaldehyde Ethyl 7-bromo-3,4,5,6-tetrahydro-4-methylthieno-[4,3,2-ef][3]benzazepine-2-carboxylate, prepared as in Example 36, is heated with cuprous cyanide in dimethylformamide to give ethyl 7-cyano-3,4,5,6-tetrahydro-4-methylthieno[4,3,2-ef][3]benzazepine-2-carboxylate.

Using the general procedure of Example 22, replacing ethyl 7-chloro-4-ethoxycarbonyl-3,4,5,6-tetrahydro-thieno[4,3,2-ef][3]benzazepine-2-carboxylate with ethyl 7-cyano-3,4,5,6-tetrahydro-4-methylthieno[4,3,2-ef][3]benzazepine-2-carboxylate gives 7-cyano-3,4,5,6-tetrahydro-4-methylthieno[4,3,2-ef][3]benzazepine-2-methanol.

Using the general procedure of Example 3, replacing 7-chloro-3,4,5,6-tetrahydro-4-methylthieno[4,3,2,-ef][3]benzazepine-2-methanol with 7-cyano-3,4,5,6-tetrahydro-4-methylthieno[4,3,2-ef][3]benzazepine-2-methanol gives 7-cyano-3,4,5,6-tetrahydro-4-methyl-thieno[4,3,2-ef][3]benzazepine2-carboxaldehyde.

EXAMPLE 39

Ethyl
9-Chloro-3,4,5,6-tetrahydro-4-methylthieno[4,3,2-ef][3]benzazepine-2-carboxylate,
9-Chloro-3,4,5,6-tetrahydro-4-methylthieno[4,3,2-ef][3]benzazepine-2-methanol, and
9-Chloro-3,4,5,6-tetrahydro-4-methylthieno[4,3,2-ef][3]benzazepine-2-carboxaldehyde Using the general of procedure of Example 34, replacing 4-fluorothiophenol with 2-chlorothiophenol gives ethyl 9-chloro-3,4,5,6-tetrahydro-4-methylthieno-[4,3,2-ef][3]benzazepine-2-carboxylate, 9-chloro-3,4,5,6-tetrahydro-4-methylthieno[4,3,2-ef][3]benzazepine-2-methanol and 9-chloro-3,4,5,6-tetrahydro-4-methyl-thieno-[4,3,2-ef][3]benzazepine-2-carboxaldehyde.

EXAMPLE 40

7-Chloro-3,4,5,6-tetrahydro-N,N,4-trimethylthieno-[4,3,2-ef][3]benzazepine-2-sulfonamide 7-Chloro-3,4,5,6-tetrahydro-4-methylthieno-[4,3,2-ef][3]benzazepine, prepared as in Example 11, is treated with excess chlorosulfonic acid and the mixture is carefully poured into ice water and carefully treated with dimethylamine to give 7-chloro-3,4,5,6-tetrahydro-N,N,4-trimethylthieno[4,3,2-ef][3]benzazepine-2-sulfonamide.

EXAMPLE 41

Diethyl
(7-Chloro-3,4,5,6-tetrahydro-4-methylthieno-[4,3,2-ef][3]benzazepine-2-yl)phosphonate 2-Bromo-7-chloro-3,4,5,6-tetrahydro-4-methyl-thieno-[4,3,2-ef][3]benzazepine, prepared as in Example 23, is treated with butyllithium in ethyl ether and then with diethyl chlorophosphate to give diethyl (7-chloro-3,4,5,6-tetrahydro-4-methylthieno-[4,3,2-ef][3]benzazepine-2-yl)phosphonate.

EXAMPLE 42

7-Chloro-3,4,5,6-tetrahydro-4-methyl-2-(methylthio)-thieno[4,3,2-ef][3]benzazepine A solution of 7-chloro-3,4,5,6-tetrahydro-4-methyl-thieno[4,3,2-ef][3]benzazepine (0.7 g, 3 mmol) in tetrahydrofuran (40 ml) was stirred at −78° C. and treated with butyllithium in tetrahydrofuran (2.5 N, 1.8 ml, 4.5 mmol) to give 7-chloro-3,4,5,6-tetrahydro-2-lithio-4-methylthieno[4,3,2-ef][3]benzazepine.

A solution of 7-chloro-3,4,5,6-tetrahydro-2-lithio-4-methylthieno[4,3,2-ef][3]benzazepine was treated with a solution of methyl disulfide (0.75 g, 8 mmol) in tetrahydrofuran (10 ml). The mixture was allowed to warm to 25° C., stirred for 30 minutes, treated with water and extracted with ethyl ether. The organic phase was dried with magnesium sulfate, concentrated in vacuo and the residue dissolved in ethyl ether and treated with hydrogen chloride to give 0.35 g (37%) of 7-chloro-3,4,5,6-tetrahydro-4-methyl-2-(methylthio)thieno[4,3,2-ef][3]-benzazepine hydrochloride: mp 220° C. (d).

EXAMPLE 43

7-Chloro-3,4,5,6-tetrahydro-4-methyl-2-(phenyl)-thieno[4,3,2-ef][3]benzazepine

Using the general procedure of Example 42, replacing methyl disulfide with tributyltin chloride, gave tributyl-[2-(7-chloro-3,4,5,6-tetrahydro-4-methylthieno-[4,3,2-ef][3]benzazepin-2-yl)]stannane.

A solution of tributyl-[2-(7-chloro-3,4,5,6-tetrahydro-4-methylthieno[4,3,2-ef][3]benzazepin-2-yl)]-stannane (0.27 g, 0.5 mmol) and iodobenzene (0.1 g, 0.5 mmol) in tetrahydrofuran (25 ml) was treated with bis(triphenylphosphine)palladium(II) chloride (19 mg) and heated to reflux for 48 hours. The mixture was treated with water, extracted with ethyl ether and the orqanic phase was dried with magnesium sulfate and concentrated in vacuo. The residue was chromatographed on a preparative silica gel plate eluted with ethyl ether-hexane (2:1) to give an oil. The oil was dissolved in ethyl ether and treated with hydrogen chloride to give 7-chloro-3,4,5,6-tetrahydro-4-methyl-2-(phenyl)thieno[4,3,2-ef][3]benzazepine hydrochloride.

EXAMPLE 44

7-Chloro-3,4,5,6-tetrahydro-$\alpha$,4-dimethylthieno[4,3,2-ef][3]benzazepine-2-methanol Sodium borohydride (0.2 g, 5 mmol) was added to a solution of 2-acetyl-7-chloro-3,4,5,6-tetrahydro-4-methylthieno[4,3,2-ef][3]benzazepine, prepared as in Example 10, (0.2 g. 0.7 mmol) in methanol (30 ml) stirred at 0° C. The mixture was stirred for 2 hours, diluted with water and extracted with ethyl ether. The organic phase was dried with magnesium sulfate and concentrated in vacuo to give 7-chloro-3,4,5,6-tetrahydro-$\alpha$,4-dimethylthieno-[4,3,2-ef][3]benzazepine-2-methanol: mp 167°-168° C.

EXAMPLE 45

7-Chloro-3,4,5,6-tetrahydro-$\alpha,\alpha$,4-trimethyl-thieno[4,3,2-ef][3]benzazepine-2-methanol Methylmagnesium bromide in tetrahydrofuran (3M, 15 ml, 45 mmol) was added to a solution of ethyl 7-chloro-3,4,5,6-tetrahydro-4-methylthieno[4,3,2-ef][3]-benzazepine-2-carboxylate, prepared as in Example 1, (3.09 g, 10 mmol) in tetrahydrofuran (60 ml) stirred under argon. The mixture was stirred for 1 hour, treated with saturated aqueous ammonium chloride and extracted with ethyl ether. The organic phase was dried with magnesium sulfate and concentrated in vacuo to give an oil which was chromatographed on silica gel eluted with methanol-methylene chloride (1:10) to give 1 g of 7-chloro-3,4,5,6-tetrahydro-$\alpha,\alpha$,4-trimethyl-thieno-[4,3,2-ef][3]benzazepine-2-methanol: mp 250° C.

EXAMPLE 46

7-Chloro-2-[[4-(chloroohenyl)methoxy]methyl]]-3,4,5,6-tetrahydro-4-methylthieno[4,3,2-ef][3]benzazepine Using the general procedure of Example 19, replacing allyl iodide with 4-chlorobenzyl chloride gives 7-chloro-2[[4-(chlorophenyl)methoxy]methyl]]-3,4,5,6-tetrahydro-4-methylthieno[4,3,2-ef][3]benzazepine hydrochloride.

EXAMPLE 47

7-Chloro-3,4,5,6-tetrahydro-4-methylthieno[4,3,2-ef][3]benzazepine-2-carboxamide Using the general procedure of Example 7, replacing dimethylamine with ammonia, gave 7-chloro-3,4,5,6-tetrahydro-4-methylthieno[4,3,2-ef][3]benzazepine-2-carboxamide: mp 203°-204° C.

EXAMPLE 48

7-Chloro-3,4,5,6-tetrahydro-4-methyl-2-(1-methylethyl)thieno[4,3,2-ef][3]benzazepine Triethylamine (2 ml) and methanesulfonyl chloride (1.1 g, 10 mmol) were added to a solution of 7-chloro-3,4,5,6-tetrahydro-$\alpha,\alpha$,4-trimethylthieno-[4,3,2-ef][3]benzazepine-2-methanol, prepared as in Example 45, (0.7 g, 2.3 mmol) in methylene chloride (50 ml) stirred at 0° C. The mixture was stirred for 3 hours, diluted with water and basified with 10% aqueous sodium hydroxide. The organic phase was dried with magnesium sulfate and concentrated in vacuo to give an oil. The oil was dissolved in ethyl ether and treated with ethereal hydrogen chloride to give 7-chloro-3,4,5,6-tetrahydro-4-methyl-2-(1-methylethenyl)thieno[4,3,2-ef][3]benzazepine hydrochloride: mp 203°-205° C. (d).

Using the general procedure of Example 13, replacing 7-chloro-2-ethenyl-3,4,5,6-tetrahydro-4-methylthieno[4,3,2-ef][3]benzazepine hydrochloride with 7-chloro-3,4,5,6-tetrahydro-4-methyl-2-(1-methylethenyl)-thieno[4,3,2-ef][3]benzazepine hydrochloride, gave 7-chloro-3,4,5,6-tetrahydro-4-methyl-2-(1-methylethyl)-thieno[4,3,2-ef][3]benzazepine: mp 225° C.

EXAMPLE 49

7-Chloro-3,4,5,6-tetrahydro-4-methyl-2-(propyl)-thieno[4,3,2-ef][3]benzazepine

Using the general procedure of Example 13, replacing methyltriphenylphosphonium bromide with ethyltriphenylphosphonium bromide gave 7-chloro-3,4,5,6-tetrahydro-4-methyl-2-(propyl)thieno[4,3,2-ef][3]benzazepine hydrochloride: mp 144°-145° C.

EXAMPLE 50

2,7-Dichloro-3,4,5,6-tetrahydro-4-methylthieno[4,3,2-ef][3]benzazepine

Using the general procedures of Example 1, Method B, iii, v and vi, replacing carbon dioxide with N-chlorosuccinimide, gave 2,7-dichloro-3,4,5,6-tetrahydro-4-methylthieno[4,3,2-ef][3]benzazepine hydrochloride: mp 225° C.

EXAMPLE 51

An oral dosage form for administering the presently invented compounds is produced by screening, mixing, and filling into a hard gelatin capsule ingredients in the proportions shown in Table II, below.

TABLE II

| Ingredients | Amounts |
| --- | --- |
| Ethyl 7-Chloro-3,4,5,6-tetrahydro-4-methylthieno[4,3,2-ef][3]benzazepine-2-carboxylate | 50 mg |
| magnesium stearate | 5 mg |
| lactose | 75 mg |

EXAMPLE 52

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
| --- | --- |
| Methyl 7-Chloro-3,4,5,6-tetrahydro-4-methylthieno[4,3,2-ef]-3-benzazepine-2-carboxylate | 100 mg |
| calcium sulfate dihydrate | 150 mg |
| sucrose | 20 mg |
| starch | 10 mg |
| talc | 5 mg |
| stearic acid | 3 mg |

EXAMPLE 53

7-Chloro-3,4,5,6-tetrahydro-4-methyl-2-[(2-propenyloxy)methyl]thieno[4,3,2-ef][3]benzazepine, 75 mg, is dispersed in 25 ml of normal saline to prepare an injectable preparation.

Contemplated equivalents of Formula (I) compounds are compounds that upon administration to mammals, including humans, are metabolized to Formula (I) compounds or metabolized to any Formula (I) compound active metabolites at a sufficient rate and in sufficient amounts to produce physiologic activity of Formula (I) compounds. Such compounds also would be included in the invented pharmaceutical compositions and used in the invented methods.

While the preferred embodiments of the invention are illustrated by the above, the invention is not limited to the precise instructions herein disclosed and that the right to all modifications coming within the scope of the following claims is reserved.

What is claimed is:

1. A compound represented by the formula:

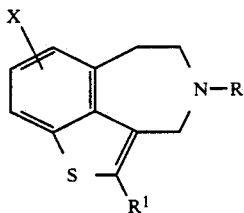

in which:

X is H, Cl, Br, F, I, $CF_3$, $C_{1-6}$alkyl, $COR^{10}$, $CO_2R^{10}$, $CONR^{16}R^{11}$, CN, $NO_2$, $Nr^{12}R^{13}$, $OR^{12}$, $SC_{1-4}$alkyl, $S(CH_2)_{0-6}$aryl, $SCF_3$, or any accessible combination thereof of up to three substituents;

R is H, $C_{1-6}$alkyl, or $C_{3-5}$alkenyl;

$R^1$ is W, $(CH_2)_{0-2}CWYZ$, or $C_{3-5}$alkenyl, except where the double bond is in the 1 position;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

each $R^{13}$ independently is H or $C_{1-6}$alkyl;

$R^{14}$ and $R^{15}$ independently are $C_{1-6}$alkyl or $(CH_2)_{0-6}$aryl;

W is H, $NO_2$, $C_{1-6}$alkyl, $CH_2CH_2OH$, CN, $C(R^{13})_2(OR^2)$, $CH_2OR^2$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I, $CF_3$, or $(CH_2)_{0-6}$aryl;

Y and Z independently are H or $C_{1-6}$alkyl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

2. A compound of claim 1 having the formula:

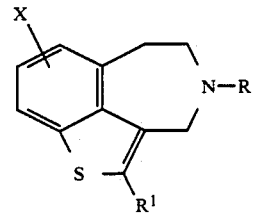

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, or $SCF_3$;

R is H, $C_{1-6}$alkyl, or $C_{3-5}$alkenyl;

$R^1$ is W, $(CH_2)_{0-2}CWYZ$, or $C_{3-5}$alkenyl, except where the double bond is in the 1-position;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl, $R^{12}$ is H, $C_{1-6}$alkyl, $COR^{14}$, or $SO_2R^{15}$;

each $R^{13}$ independently is H or $C_{1-6}$alkyl;

$R^{14}$ and $R^{15}$ independently are $C_{1-6}$alkyl or $(CH_2)_{0-6}$aryl;

W is H, $NO_2$, $C_{1-6}$alkyl, $CH_2CH_2OH$, CN, $C(R^{13})_2(OR^2)$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I, $CF_3$, or $(CH_2)_{0-6}$aryl;

Y and Z independently are H or $C_{1-6}$alkyl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

3. A compound of claim 2 wherein X is Cl, Br, F, or I.

4. A compound of claim 3 wherein R is $CH_3$.

5. A compound of claim 4 that is 7-chloro-2-ethyl-3,4,5,6-tetrahydro-4-methylthieno[4,3,2-ef]-[3]benzazepine, or a pharmaceutically acceptable salt thereof.

6. A compound of claim 4 that is:

ethyl 7-chloro-3,4,5,6-tetrahydro-4-methylthieno[4,3,2-ef][3]benzazepine-2-carboxylate;

7-chloro-3,4,5,6-tetrahydro-4-methylthieno-[4,3,2-ef][3]benzazepine-2-methanol;

7-chloro-3,4,5,6-tetrahydro-4-methylthieno-[4,3,2-ef][3]benzazepine-2-carboxaldehyde;

methyl 7-chloro-3,4,5,6-tetrahydro-4-methyl-thieno[4,3,2-ef][3]benzazepine-2-carboxylate;

7-chloro-3,4,5,6-tetrahydro-4-methyl-2-[(2-propenyloxy)methyl]thieno[4,3,2-ef][3]benzazepine;

7-chloro-3,4,5,6-tetrahydro-4-methylthieno-[4,3,2-ef][3]benzazepine;

7-chloro-3,4,5,6-tetrahydro-2,4-dimethylthieno[4,3,2-ef][3]benzazepine;

7-chloro-3,4,5,6-tetrahydro-4-methylthieno-[4,3,2-ef][3]benzazepine-2-ethan-2-ol;

7-chloro-3,4,5,6-tetrahydro-4-methylthieno-[4,3,2-ef][3]benzazepine-2-ethan-2-one;

7-chloro-3,4,5,6-tetrahydro-4-methylthieno-[4,3,2-ef][3]benzazepine-2-carboxamide;

N,N-dimethyl-7-chloro-3,4,5,6-tetrahydro-4-methylthieno[4,3,2-ef][3]-2-benzazepine-carboxamide;

7-chloro-3,4,5,6-tetrahydro-4-methyl-2-(1-methyethyl)-thieno[4,3,2-ef][3]benzazepine;

7-chloro-2-propyl-3,4,5,6-tetrahydro-4-methyl-thieno[4,3,2-ef][3]benzazepine; or 2,7-dichloro-3,4,5,6-tetrahydro-4-methylthieno[4,3,2-ef][3]benzazepine;

or a pharmaceutically acceptable salt thereof.

7. A pharmaceutical composition comprising a compound of claim 1 and a suitable pharmaceutical carrier.

8. A pharmaceutical composition of claim 7 wherein the compound is 7-chloro-2-ethyl-3,4,5,6-tetrahydro-4-methylthieno[4,3,2-ef][3]benzazepine.

9. A pharmaceutical composition of claim 7 wherein the compound is:

ethyl 7-chloro-3,4,5,6-tetrahydro-4-methylthieno[4,3,2-ef][3]benzazepine-2-carboxylate;

7-chloro-3,4,5,6-tetrahydro-4-methylthieno[4,3,2-ef][3]benzazepine-2-methanol;

7-chloro-3,4,5,6-tetrahydro-4-methylthieno[4,3,2-ef][3]benzazepine-2-carboxaldehyde;

methyl 7-chloro-3,4,5,6-tetrahydro-4-methyl-thieno[4,3,2-ef][3]benzazepine-2-carboxylate;

7-chloro-3,4,5,6-tetrahydro-4-methyl-2-[(2-propyloxy)-methyl]thieno[4,3,2-ef][3]benzazepine 7-chloro-3,4,5,6-tetrahydro-4-methylthieno[4,3,2-ef][3]benzazepine;

7-chloro-3,4,5,6-tetrahydro-2,4-dimethylthieno[4,3,2-ef][3]benzazepine;

7-chloro-3,4,5,6-tetrahydro-4-methylthieno[4,3,2-ef][3]benzazepine-2-ethan-2-ol;

7-chloro-3,4,5,6-tetrahydro-4-methylthieno[4,3,2-ef][3]benzazepine-2-ethan-2-one;

7-chloro-3,4,5,6-tetrahydro-4-methylthieno[4,3,2-ef][3]benzazepine-2-carboxamide;

N,N-dimethyl-7-chloro-3,4,5,6-tetrahydro-4-methyl-thieno[4,3,2-ef][3]-2-benzazepine-carboxamide;

7-chloro-3,4,5,6-tetrahydro-4-methyl-2-(1-methylethyl)thieno[4,3,2-ef][3]benzazepine;

7-chloro-2-propyl-3,4,5,6-tetrahydro-4-methyl-thieno[4,3,2-ef][3]benzazepine; or 2,7-dichloro-3,4,5,6-tetrahydro-4-methylthieno[4,3,2-ef][3]benzazepine.

10. A method of antagonizing α-adrenergic receptors in mammals that comprises administering to a subject in need thereof an effective amount of a compound of claim 1.

11. A method of claim 10 wherein the compound is 7-chloro-2-ethyl-3,4,5,6-tetrahydro-4-methyl-thieno[4,3,2-ef][3]benzazepine.

12. A method of claim 10 wherein the compound is:

ethyl 7-chloro-3,4,5,6-tetrahydro-4-methylthieno[4,3,2-ef][3]benzazepine-2-carboxylate;

7-chloro-3,4,5,6-tetrahydro-4-methylthieno[4,3,2-ef][3]benzazepine-2-methanol;

7-chloro-3,4,5,6-tetrahydro-4-methylthieno[4,3,2-ef][3]benzazepine-2-carboxaldehyde;

methyl 7-chloro-3,4,5,6-tetrahydro-4-methyl-thieno[4,3,2-ef][3]benzazepine-2-carboxylate;

7-chloro-3,4,5,6-tetrahydro-4-methyl-2-[(2Propenyloxy)methyl]thieno[4,3,2-ef][3]benzazepine;

7-chloro-3,4,5,6-tetrahydro-4-methylthieno-[4,3,2-ef][3]benzazepine;

7-chloro-3,4,5,6-tetrahydro-2,4-dimethylthieno[4,3,2-ef][3]benzazepine;

7-chloro-3,4,5,6-tetrahydro-4-methylthieno-[4,3,2-ef][3]benzazepine-2-ethan-2-ol;

7-chloro-3,4,5,6-tetrahydro-4-methylthieno-[4,3,2-ef][3]benzazepine-2-ethan-2-one;

7-chloro-3,4,5,6-tetrahydro-4-methylthieno-[4,3,2-ef][3]-benzazepine-2-carboxamide;

N,N-dimethyl-7-chloro-3,4,5,6-tetrahydro-4-methyl-thieno[4,3,2-ef][3]-2-benzazepine-carboxamide;

7-chloro-3,4,5,6-tetrahydro-4-methyl-2-(1-methylethyl)thieno[4,3,2-ef][3]benzazepine;

7-chloro-2-propyl-3,4,5,6-tetrahydro-4-methyl-thieno[4,3,2-ef][3]benzazepine; or 2,7-dichloro-3,4,5,6-tetrahydro-4-methylthieno[4,3,2-ef][3]benzazepine.

13. A method of reducing blood pressure in mammals that comprises administering to a subject in need thereof an effective amount of a compound of claim 1.

14. A method of treating benign prostatic hypertrophy in mammals that comprises administering to a subject in need thereof an effective amount of a compound of claim 1.

15. A method of treating peripheral vascular disease in mammals that comprises administering to a subject in need thereof an effective amount of a compound of claim 1.

16. A method of treating congestive heart failure in mammals that comprises administering to a subject in need thereof an effective amount of a compound of claim 1.

17. a compound of claim 4 that is 7-chloro-3,4,5,6-tetrahydro-4-methyl-2-(methylthio)thieno[4,3,2,-ef][3]-benzazepine, or a pharmaceutically acceptable salt thereof.

18. A pharmaceutical composition of claim 7 wherein the compound is 7-chloro-3,4,5,6-tetrahydro-4-methyl-2-(methylthio)thieno[4,3,2-ef][3]benzazepine.

19. A method of claim 10 wherein the compound is 7-chloro-3,4,5,6-tetrahydro-4-methyl-2-(methylthio)-thieno[4,3,2-ef][3]benzazepine.

* * * * *

UNITED STATES PATENT AND TRADEMARK OFFICE
CERTIFICATE OF CORRECTION

PATENT NO. : 5,006,521

DATED : April 9, 1991

INVENTOR(S) : Lafferty, DeMarinis, Shah

Page 1 of 2

It is certified that error appears in the above-identified patent and that said Letters Patent is hereby corrected as shown below:

In claim 1, column 34, line 16; replace "or $CH_2)_{0-6}$arlyl;" to --- or $(CH_2)_{0-6}$arlyl; ---.

In claim 2, column 34, lines 20 to 30; replace
"
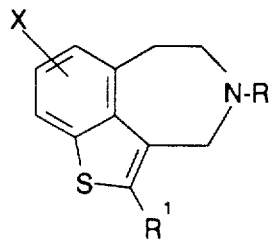
"

with ---
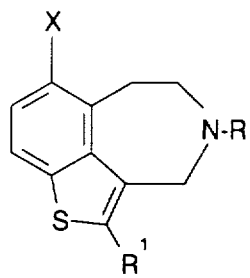
---.

UNITED STATES PATENT AND TRADEMARK OFFICE
CERTIFICATE OF CORRECTION

PATENT NO. : 5,006,521

DATED : April 9, 1991

INVENTOR(S) : Lafferty, DeMarinis, Shah

It is certified that error appears in the above-identified patent and that said Letters Patent is hereby corrected as shown below:

In claim 12, column 36, line 17; replace "2-[(2Propenylox" with --- 2-[(2-propenylox ---.

Signed and Sealed this

Tenth Day of August, 1993

Attest:

MICHAEL K. KIRK

*Attesting Officer*     *Acting Commissioner of Patents and Trademarks*